(12) United States Patent
Shimada et al.

(10) Patent No.: US 10,539,571 B2
(45) Date of Patent: Jan. 21, 2020

(54) METHOD FOR PREPARING PEPTIDE FRAGMENTS, KIT FOR PREPARING PEPTIDE FRAGMENTS TO BE USED THEREIN, AND ANALYSIS METHOD

(71) Applicant: SHIMADZU CORPORATION, Kyoto-shi (JP)

(72) Inventors: Takashi Shimada, Kyoto (JP); Noriko Fukao, Kyoto (JP); Chikage Aoki, Kyoto (JP); Taka-Aki Sato, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 317 days.

(21) Appl. No.: 15/063,774

(22) Filed: Mar. 8, 2016

(65) Prior Publication Data

US 2016/0252522 A1    Sep. 1, 2016

Related U.S. Application Data

(63) Continuation of application No. PCT/JP2013/074292, filed on Sep. 9, 2013.

(51) Int. Cl.
| | |
|---|---|
| *C07K 17/00* | (2006.01) |
| *C12N 11/00* | (2006.01) |
| *C12P 21/06* | (2006.01) |
| *G01N 1/40* | (2006.01) |
| *G01N 33/68* | (2006.01) |

(52) U.S. Cl.
CPC ......... *G01N 33/6857* (2013.01); *C07K 17/00* (2013.01); *C12N 11/00* (2013.01); *C12P 21/06* (2013.01); *G01N 1/405* (2013.01); *G01N 33/6851* (2013.01); *G01N 2333/948* (2013.01);
(Continued)

(58) Field of Classification Search
CPC ..... C12P 21/06; G01N 1/405; G01N 33/6857; G01N 33/948–976
See application file for complete search history.

(56) References Cited

U.S. PATENT DOCUMENTS

| | | | | |
|---|---|---|---|---|
| 4,071,409 | A * | 1/1978 | Messing | A61K 39/44 435/176 |
| 7,258,990 | B2 * | 8/2007 | Falcovitz-Gerassi | G01N 33/543 422/417 |

(Continued)

FOREIGN PATENT DOCUMENTS

| | | | |
|---|---|---|---|
| EP | 3023777 A1 | * | 5/2016 |
| JP | 2004-518944 A | | 6/2004 |

(Continued)

OTHER PUBLICATIONS

Sigma-Aldrich Particle Size Conversion Table, from p. T848 of the Aldrich 2003-2004 Catalog/Handbook of Fine Chemicals. (Year: 2003).*

(Continued)

*Primary Examiner* — Jeffrey E. Russel
(74) *Attorney, Agent, or Firm* — Oblon, McClelland, Maier & Neustadt, L.L.P.

(57) ABSTRACT

A method of proteolyzing a protein, including immobilizing a protein in at least one pore of a porous body, and contacting the protein immobilized in the pore and a protease immobilized on a solid surface such that the protease selectively accesses a site of the protein and proteolyzes the protein at the site.

14 Claims, 11 Drawing Sheets

Specification includes a Sequence Listing.

(52) U.S. Cl.
CPC ... *G01N 2333/976* (2013.01); *G01N 2560/00* (2013.01)

(56) References Cited

U.S. PATENT DOCUMENTS

| | | |
|---|---|---|
| 2010/0015652 A1 | 1/2010 | Granda et al. |
| 2010/0063256 A1* | 3/2010 | Spector .................. C07K 1/22 530/387.1 |

FOREIGN PATENT DOCUMENTS

| | | | |
|---|---|---|---|
| JP | 2011-130749 A | 7/2011 | |
| WO | WO-9009237 A1 * | 8/1990 | ............ B01J 20/286 |
| WO | WO 02/05930 A1 | 1/2002 | |
| WO | WO 2008/079914 A1 | 7/2008 | |
| WO | WO 2015033479 A1 * | 3/2015 | |
| WO | WO 03/087821 A2 | 10/2018 | |

OTHER PUBLICATIONS

Fei Xu et al., "Facile Trypsin Immobilization in Polymeric Membranes for Rapid, Efficient Protein Digestion", Analytical Chemistry, vol. 82, No. 24, 2010, 10045-10051.

Qianhao Min et al., "Size-selective proteolysis on mesoporous silica-based trypsin nanoreactor for low-MW proteome analysis", Chemical Communication, vol. 46, 2010, 6144-6146.

International Search Report dated Nov. 12, 2013, in PCT/JP2013/074292, filed Sep. 9, 2013.

Office Action dated Aug. 2, 2018 in Indian Patent Application No. 201617001768 (with English translation), 7 pages.

\* cited by examiner

1. ProteinG-IgG / FG beads-Trypsin 5μg
2. ProteinG-IgG / FG beads-Trypsin 10μg
3. ProteinG-IgG / FG beads-Trypsin 25μg
4. ProteinG / FG beads-Trypsin 5μg
5. ProteinG / FG beads-Trypsin 10μg
6. ProteinG / FG beads-Trypsin 25μg
7. FG beads-Trypsin 5ug
8. FG beads-Trypsin 10ug Fig. 11A Herceptin H-Chain

```
                                    CDR1                        CDR2
EVQLVESGGG  LVQPGGSLRL  SCAA SGFNIK  DTYIHWVR QA  PGKGLE WVAR  IYPTNGYTRY
ADSVKGRFTI  SADTSKNTAY  LQMNSLRAED  TAVY YCSRWG  GDGFYAMDYW  GQGTLVTVSS
                                          CDR3
ASTKGPSVFP  LAPSSKSTSG  GTAALGCLVK  DYFPEPVTVS  WNSGALTSGV  HTFPAVLQSS
GLYSLSSVVT  VPSSSLGTQT  YICNVNHKPS  NTKVDKKVEP  KSC
```

Fig. 11B Herceptin L-Chain

```
                                    CDR1                        CDR2
DIQMTQSPSS  LSASVGDRVT  ITC RASQDVN  TAVAWYQQ KP  GKAPK LIYS  ASFLYSGVPS
RFSGSRSGTD  FTLTISSLQP  EDFATY YCQQ  HYTTPPTFGQ  GTKVE KRTV  AAPSVFIFPP
                                CDR3
SDEQLKSGTA  SVVCLLNNFY  PREAKVQWKV  DNALQSGNSQ  ESVTEQDSKD  STYSLSSTLT
LSKADYEKHK  VYACEVTHQG  LSSPVTKSFN  RGEC
```

Fig. 12

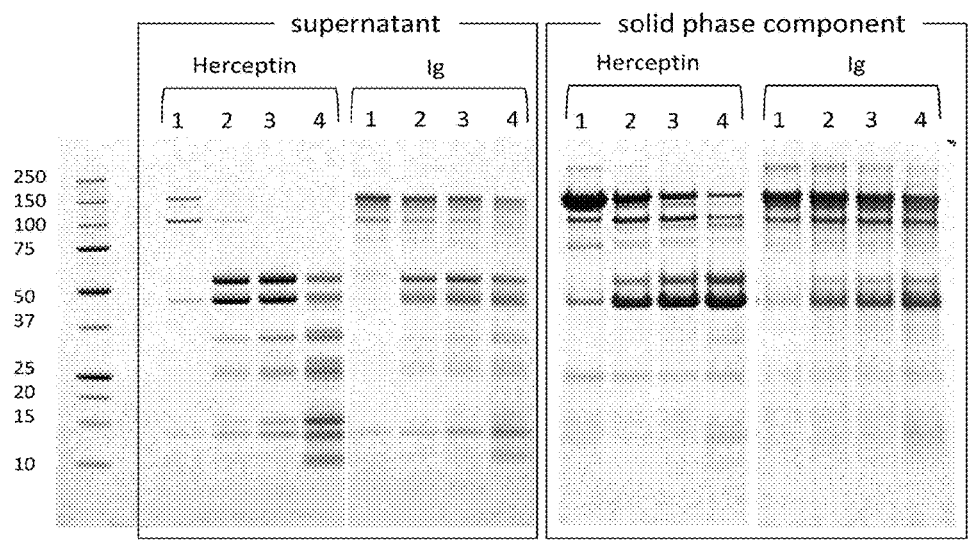

METHOD FOR PREPARING PEPTIDE FRAGMENTS, KIT FOR PREPARING PEPTIDE FRAGMENTS TO BE USED THEREIN, AND ANALYSIS METHOD

CROSS-REFERENCE TO RELATED APPLICATIONS

The present application is a continuation of International Application No. PCT/JP2013/074292, filed Sep. 9, 2013. The entire contents of this application are incorporated herein by reference.

BACKGROUND OF THE INVENTION

Field of the Intention

The present invention relates to a method for preparing peptide fragments by site-selectively proteolyzing a protein, such as an antibody, using a protease, and a kit for preparing peptide fragments to be used therein. Further, the present invention relates to a method for analyzing peptide fragments, prepared by the method, by mass spectrometry or the like to detect or quantitate a protein.

Discussion of the Background

A method has been developed in which a protein to be analyzed is subjected to site-selective proteolysis to reduce the number (of types) of peptide fragments in a sample to improve the accuracy of analysis and simplify the process of analysis. For example, WO 2008/079914 proposes a method in which an antibody is subjected to pepsin digestion to produce an F(ab')$_2$ fragment, and then the F(ab')$_2$ fragment is further digested with a protease such as trypsin to produce peptide fragments containing the complementarity-determining region (CDR) of the antibody, and the peptide fragments containing CDR are detected and quantitated by mass spectrometry. JP 2011-130749 A reports that combined use of pepsin or papain and a specific ion improves the efficiency of proteolysis with such a protease.

Fei Xu et. al., *Anal. Chem.*, 2010, 82, 10045-10051 report an example in which the efficiency of trypsin digestion of albumin is increased by allowing an albumin solution to pass through a nylon porous membrane having trypsin immobilized in pores thereof. Qianhao Min et. al., *Chem. Commun.*, 2010, 46(33), 6144-6146 report that a protein having a small molecular weight can be selectively subjected to trypsin digestion by using mesoporous silica having trypsin immobilized in pores thereof.

Hereinafter, the structure of an antibody will be described. All antibodies have two heavy chains (H chains) and two light chains (L chains). One light chain and one heavy chain are linked through a disulfide (S—S) bond to form a heterodimer, and the two heterodimers are further linked through two disulfide bonds to form a "Y"-shaped heterotetramer (see FIG. 2). An antibody has one Fc (Fragment, crystallizable) domain comprising heavy chains and two Fab (Fragment, antigen binding) domains comprising a heavy chain and a light chain, and the Fc domain and the Fab domains are linked through a hinge region.

The Fc domain of an antibody mainly has the function of initiating a reaction after the antibody binds to an antigen (effector function), and most of antibodies derived from the same species have a common amino acid sequence in the Fc domain. On the other hand, the end (on the N-terminal side) of the Fab domain has the function of binding to an antigen. The N-terminal part of the Fab domain diversely changes in its amino acid sequence so as to be able to bind to various antigens. This region is called variable region (V region), and the variable region of the light chain and the variable region of the heavy chain are called VL region and VH region, respectively. The Fab and Fc domains other than the V region are called constant region (C region) that varies little in amino acid sequence. The constant region of the light chain is called CL region, and the constant region of the heavy chain is called CH region. The CH region is further divided into three regions, CH1 region, CH2 region, and CH3 region. The Fab domain of the heavy chain comprises the VH region and the CH1 region, and the Fc domain of the heavy chain comprises CH2 and CH3. The hinge region is located between CH1 and CH2.

The specificity (i.e., specific bindability to an antigen) of an antibody is determined by the combination of amino acid sequences of the V region. The light chain and the heavy chain each have three complementarity-determining regions (CDRs) in the V region of the Fab domain. CDR is also called hypervariable region, and varies in amino acid sequence depending on the type of antibody. There are 3 CDRs on each of the heavy and light chains of an antibody (6 types of CDRs in total), which creates diversity that allows the antibody to bind to various antigens. In other words, CDRs are regions characterizing an antibody, and therefore an antibody can be identified by identifying the amino acid sequences of CDRs thereof.

As described above, the Fab domains and Fc domain of an antibody are linked through a hinge region. Papain which is a kind of protease proteolyzes the hinge region, and therefore two Fab domains and one Fc domain are produced by papain digestion of an antibody. Further, pepsin which is a kind of protease proteolyzes one of the two disulfide bonds, i.e., the Fc domain-side (C-terminal side) disulfide bond of the hinge region, and therefore an F(ab')$_2$ domain having two Fab domains linked together and many Fc domain fragments are produced by pepsin digestion.

SUMMARY OF THE INVENTION

According to one aspect of the present invention, a method of proteolyzing a protein includes immobilizing a protein in at least one pore of a porous body, and contacting the protein immobilized in the pore and a protease immobilized on a solid surface such that the protease selectively accesses a site of the protein and proteolyzes the protein at the site.

According to another aspect of the present invention, a kit for proteolyzing a protein includes a porous body having pores in which a protein is to be immobilized, and particles having an average particle diameter larger than an average pore diameter of the pores, wherein the particles have a surface on which a protease has been immobilized or to be immobilized.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 11A and 11B show the amino acid sequences of heavy and light chains of trastuzumab, respectively, wherein peptide fragments identified by mass spectrometry in this experiment are underlined. FIG. 11A shows SEQ ID NO: 1, and FIG. 11B shows SEQ ID NO: 2.

FIG. 12 shows electrophoretic patterns obtained in an experiment for studying mixed protease proteolysis.

DESCRIPTION OF THE EMBODIMENTS

Figure 1:
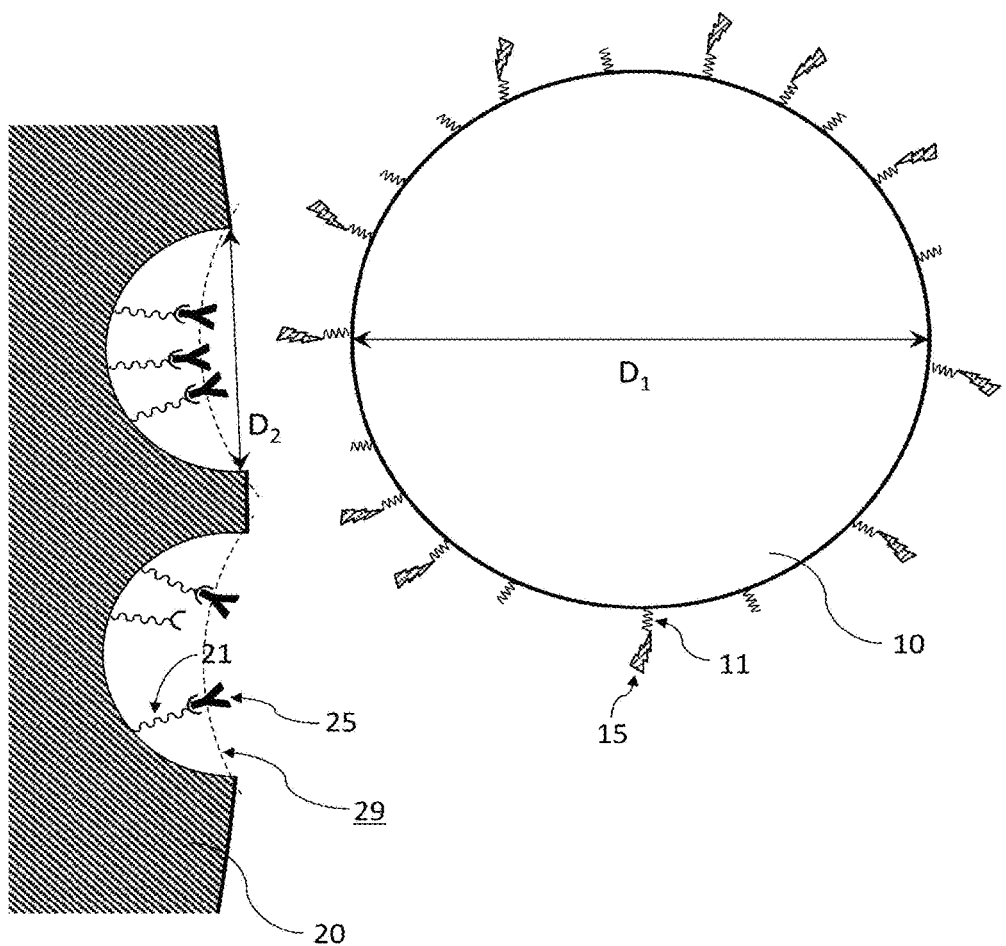
FIG. 1 is a conceptual diagram for illustrating the principle of site-selective proteolysis according to an aspect of the present invention.
Figure 2:
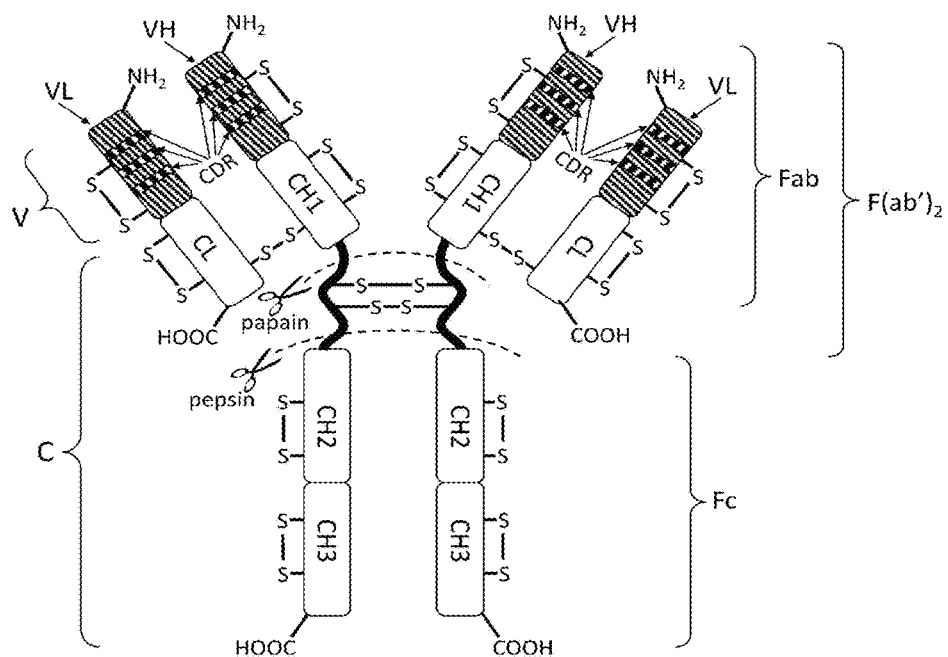
FIG. 2 is a schematic diagram for illustrating the structure of an antibody.

The embodiments will now be described with reference to the accompanying drawings, wherein like reference numerals designate corresponding or identical elements throughout the various drawings.

In a method for preparing peptide fragments according to an aspect of the present invention, a substrate protein to be proteolyzed is immobilized in pores of a porous body, and the porous body having the substrate protein immobilized thereon is brought, in a liquid, into contact with fine particles having a protease immobilized on a surface thereof. FIG. 1 is a conceptual diagram for illustrating the principle of protease proteolysis according to an aspect of the present invention.

On the surface of fine particles 10 (average particle diameter $D_1$), a protease 15 is immobilized. A porous body 20 has a plurality of pores 29 (average pore diameter $D_2$), and a substrate protein 25 is immobilized in the pores. In the method according to an aspect of the present invention, as described above, both the protease 15 and the substrate protein 25 are immobilized on solid phases in a small region, and protease proteolysis is performed by contact between the solid phases.

The average particle diameter $D_1$ of the fine particles 10 is larger than the average pore diameter $D_2$ of the porous body 20. Therefore, the fine particles 10 can access the shallow parts (opening portions) of the pores 29 and their vicinity, but cannot access the deep parts of the pores 29. As a result, the protease 15 immobilized on the surface of the fine particles 10 cannot access the deep parts of the pores 29. In FIG. 1, a dotted line near each of the pores 29 indicates the limit of the region accessible to protease 15.

In this way, the accessibility of the protease 15 to the substrate protein 25 in the pores 29 is site-selectively limited so that the relative probability of accessibility of the protease 15 to the liquid phase side ("Y"-shaped site in FIG. 1) of the substrate protein increases. This makes it possible to subject the substrate protein 25 to site-selective protease proteolysis to obtain peptide fragments.

Substrate Protein

The substrate protein 25 is a protein to be analyzed. The type of the substrate protein is not particularly limited. However, from the viewpoint of performing site-selective proteolysis, the substrate protein preferably has a molecular diameter larger than that of the protease 15. The substrate protein may be a protein complex. As the molecular diameter, a value determined based on structural analysis by X-ray or NMR is available from various documents or databases. For example, the molecular diameter of an antibody is about 15 nm. Alternatively, the molecular diameter may be determined by, for example, X-ray small angle scattering or may be roughly estimated from a molecular weight. As reference examples, Table 1 shows molecular weights and molecular diameters of proteins used as marker molecules to determine the separation properties of an ultrafiltration membrane.

TABLE 1

| protein | molecular weight [Da] | molecular diameter [nm] |
|---|---|---|
| sucrose | 340 | 1.1 |
| raffinose | 590 | 1.3 |
| vitamin B12 | 1,360 | 1.7 |
| bacitracin | 1,410 | 1.7 |
| insulin | 5,700 | 2.7 |
| cytochrome C | 13,400 | 3.8 |
| myoglobin | 17,000 | 4.0 |
| α-chymotrysinogene | 25,000 | 4.6 |
| pepsin | 35,000 | 5.0 |
| ovalbumin | 43,000 | 5.6 |
| Bovine albumin | 67,000 | 6.4 |
| aldolase | 142,000 | 8.2 |
| γ-globulin | 150,000 | 8.4 |

The substrate protein 25 is preferably one that can site-specifically bind into the pores 29 of the porous body 20. Site-specific binding of the substrate protein 25 allows a site other than the binding site to be subjected to selective protease proteolysis. For example, a protein bearing, at its C- or N-terminus, a tag sequence such as a His tag (tag peptide containing about 6 continuous histidine residues) or a biotinylated peptide, an enzyme that specifically binds with a specific substrate, or the like may also be used as the protein that can site-specifically bind.

In an aspect of the present invention, an antibody is particularly preferably used as the substrate protein that can site-specifically bind into the pores of the porous body. Immobilization of the Fc domain of the antibody on the porous body 20 allows the Fab domain of the antibody to be subjected to selective protease proteolysis. Although the type of the antibody is not particularly limited, a monoclonal antibody is preferred. Examples of the monoclonal antibody include: human antibodies such as panitumumab (Vectibix), ofatumumab (Arzerra), golimumab (Simponi), and ipilimumab (Yervoy); humanized antibodies such as tocilizumab (Actemra), trastuzumab (Herceptin), bevacizumab (Avastin), omalizumab (Xolair), mepolizumab (Bosatria), gemtuzumab ozogamicin (Mylotarg), palivizumab (Synagis), ranibizumab (Lucentis), certolizumab (Cimzia), ocrelizumab, mogamulizumab (Poteligeo), and eculizumab (Soliris); and chimeric antibodies such as rituximab (Rituxan), cetuximab (Erbitux), infliximab (Remicade), and basiliximab (Simulect). These antibodies are used as antibody drugs (molecularly-targeted drugs), and the concentrations of the antibodies in blood need to be quantitated in clinical trials or the like.

In an aspect of the present invention, the Fab domain of the monoclonal antibody can be subjected to site-selective protease proteolysis to obtain peptide fragments, and the antibody can be identified and quantitated by mass spectrometry of the obtained peptide fragments. The analysis method is a method in which peptide fragments derived from the variable region of the antibody are detected to identify (detect) or quantitate the antibody, that is, a method in which peptide fragments derived from the antibody are directly measured. Therefore, in this aspect, the analysis method requires no specific binding substance such as an antigen, and therefore can be applied irrespective of the type of antibody. Therefore, the method can be applied not only to the above-mentioned antibodies but also to newly-developed monoclonal antibodies.

Porous Body

The material of the porous body 20 is not particularly limited as long as the material has pores 29. Although the pores shown in FIG. 1 have a semi-spherical shape, the shape of the pores is not particularly limited. A porous body having through-holes, such as a porous membrane, may also be used.

For the porous body 20, activated carbon, a porous membrane, porous resin beads, metal particles, or the like may be used. Among them, one that can specifically bind with the substrate protein is preferred, and one that can site-specifically bind with the substrate protein is particularly preferred. For example, affinity column packing beads used to purify a specific protein or the like can be satisfactory.

The porous body 20 preferably used in an aspect of the present invention is one in which a linker molecule 21 that can site-specifically interact with the substrate protein 25 is immobilized in the pores 29 thereof. Examples of the interaction between the substrate protein and the linker molecule include chemical binding, hydrogen binding, ion binding, complex formation, hydrophobic interaction, van der Waals interaction, electrostatic interaction, and stereoselective interaction.

The optimum linker molecule can be appropriately selected, depending on the type or binding site of the substrate protein, from functional groups such as an amino group, a carboxyl group, and an epoxy group; labeling compounds such as biotin and digoxygenin; proteins such as avidin, streptoavidin, Protein A, Protein G, and immunoglobulin; various ligands; substrate compounds for enzymes; silica; and metal chelates.

Protein G, Protein A, or the like is preferably used as the linker molecule 21, when the substrate protein 25 is an antibody. Protein A or Protein G site-specifically binds with the Ig loop in Fc domain of the antibody. The use of the porous body 20 having the linker molecule 21, such as Protein A or Protein G, immobilized in the pores 29 allows the Fc domain of the antibody (substrate protein 25) to be site-specifically immobilized in the pores so that the Fab domain of the antibody is located on the liquid-phase side (near the opening portions of the pores). Such immobilization of the antibody in the pores in a given direction controls the orientation of the antibody in the pores, and therefore the Fab domain can be site-selectively proteolyzed with the protease.

Further, when the substrate protein is immobilized in the pores so as to be present in a small environment at the interface between the solid phase and the liquid phase, the substrate protein is likely to be denatured and molecular fluctuations are disturbed so that the probability of being attacked by the protease increases. Further, in an aspect of the present invention, the protease is immobilized on the particles, and therefore an environment is created in which the protease is sterically stable and autolysis is less likely to occur. This is considered to increase the stability of the protease. Therefore, in the method according to an aspect of the present invention, site-selective protease proteolysis can be performed, and in addition, high activity of the protease can be maintained.

The size of the pores 29 of the porous body 20 is not particularly limited. The size of the pores is preferably determined in consideration of the molecular diameter of the substrate protein etc. so that the tip of the substrate protein, i.e., the site to be selectively proteolyzed, is located near the opening portions of the pores 29 when the substrate protein 25 is immobilized. The average pore diameter $D_2$ of the porous body 20 is appropriately set to fall in the range of, for example, about 10 nm to 500 nm and to be smaller than the average particle diameter $D_1$ of the fine particles 10. The average pore diameter $D_2$ of the porous body 20 is, for example, preferably about 20 nm to 200 nm, more preferably about 30 nm to 150 nm. Particularly, when the substrate protein 25 is an antibody, in order to immobilize the Fc domain of the antibody in the pores to subject the Fab domain of the antibody to site-selective proteolysis, the pore diameter of the porous body is preferably 30 nm to 150 nm, more preferably 40 nm to 120 nm, further preferably 50 nm to 100 nm.

The size of the linker molecule is selected in consideration of the size of the pores or size of the substrate protein so that the selective proteolysis site of the substrate protein is located near the opening portions of the pores. The size of a molecule in which the linker molecule binds with the substrate protein is preferably about 0.5 to 1.5 times, more preferably about 0.6 to 1.2 times, further preferably about 0.7 to 1.1 times, particularly preferably about 0.8 to 1 times the pore diameter of the porous body. When the linker molecule is not immobilized on the porous body 20 and the substrate protein directly binds into the pores of the porous body, the molecular diameter of the substrate protein and the pore diameter of the porous body preferably satisfy the above relationship.

Immobilization of Substrate Protein

A method for immobilizing the substrate protein 25 in the pores 29 of the porous body 20 is not particularly limited, and an appropriate method can be adopted depending on the properties of the substrate protein and the porous body (or the linker molecule immobilized on the porous body) etc. For example, when the porous body has Protein A or Protein G immobilized in the pores thereof, an antibody can be easily immobilized in the pores by mixing a suspension of the porous body and a solution containing the antibody.

The quantitative ratio between the porous body and the substrate protein can be appropriately set depending on the purpose. For example, in the case of quantitative analysis of the substrate protein, it is desired that almost entire amount of the substrate protein in a sample should be immobilized on the porous body. Therefore, the quantitative ratio is preferably set so that the amount of the porous body becomes higher than the estimated amount of the substrate protein contained in the sample.

Protease

The protease 15 recognizes the amino acid sequence of the substrate protein and selectively proteolyzes a specific bond in a specific sequence. In an aspect of the present invention, the substrate protein 25 is immobilized in the pores 29 of the porous body 20, and the protease 15 proteolyzes the substrate protein 25 at a specific amino acid sequence site, so that peptide fragments are obtained.

Examples of the protease include trypsin (which proteolyzes a peptide at the C-terminal side of basic amino acid residues (Arg and Lys)), lysyl endopeptidase (which proteolyzes a peptide at the C-terminal side of a Lys residue), arginine endopeptidase (which proteolyzes a peptide at the C-terminal side of an Arg residue), chymotrypsin (which proteolyzes a peptide at the C-terminal side of aromatic amino acid residues (Phe, Tyr, and Trp)), V8 protease (which proteolyzes a peptide at the C-terminal side of a Glu residue), pepsin, and papain. Two or more of these proteases may be used in combination.

When peptide fragments of the substrate protein after protease proteolysis are subjected to mass spectrometry as a measurement sample, the protease to be used is preferably one with low autolysis and high selectivity for a sequence to be proteolyzed. When a commercially-available protease is used, a mass spectrometry-grade protease or a sequencing-grade protease is preferably used. For example, native trypsin derived from a living body has low specificity for a proteolysis site because pseudo trypsin that exhibits chymotrypsin-like activity is generated due to autolysis. Therefore, mass spectrometry-grade trypsin is commercially available which achieves high resistance to autolysis due to reductive methylation of lysine residues of trypsin.

In order to improve the site-selectivity of protease proteolysis of the substrate protease, it is important to limit the region where the protease can access the substrate protein. Therefore, the molecular diameter of the protease is preferably smaller than that of the substrate protein. More specifically, the molecular diameter of the protease is preferably 10 nm or less, more preferably 8 nm or less, further preferably 6 nm or less, particularly preferably 5 nm or less. A protein having a molecular weight of about 30 kDa, such as trypsin or lysyl endopeptidase, has a molecular diameter of about 4 nm (see Table 1 shown above).

Among the above-mentioned proteases, trypsin is particularly preferably used in an aspect of the present invention. As described above, trypsin has a small molecular diameter and its active site is present inside its molecule. This limits the region where the active site can access the substrate protein, which makes it possible to improve the site-selectivity of protease proteolysis. Particularly, when the substrate protein is an antibody, the protease to be used is preferably trypsin.

In proteome analysis study, digestion with a combination of trypsin and lysyl endopeptidase has attracted attention in recent years as a technique for improving the recovery rate of peptide fragments (*J. Proteome Res.*, 2012, 11(11), 5145-5156). The reason for this is considered to be that trypsin has the property of allowing a decomposition reaction to proceed in stages from the outside of a steric structure, and lysyl endopeptidase first proteolyzes mainly the hinge region of an antibody. In an aspect of the present invention, on the other hand, it is preferred that trypsin is used alone or that even when lysyl endopeptidase or the like is used in combination with trypsin, the amount of trypsin is preferably 90% or higher of the total amount of proteases used, in order to suppress the proteolysis of the hinge region of an antibody and to selectively proteolyze the Fab domain (more preferably, the V region of the Fab domain) of the antibody.

Fine Particles

The fine particles 10 are used for the purpose of immobilizing the protease 15 on the surface thereof to control the accessibility of the protease to the substrate protein 25 immobilized in the pores 29 of the porous body 20. Therefore, the average particle diameter $D_1$ of the fine particles 10 is preferably larger than the average pore diameter $D_2$ of the porous body 20 so that the fine particles 10 do not enter the deep part of the pores 29 of the porous body 20. The average particle diameter $D_1$ of the fine particles 10 is more preferably 1.2 times or more, further preferably 1.5 times or more, particularly preferably 1.8 times or more the average pore diameter $D_2$ of the porous body 20.

Although the shape of the fine particles 10 is not particularly limited, spherical fine particles are preferred from the viewpoint of equalizing the accessibility of the protease to the pores 29 of the porous body 20. Further, the fine particles 10 preferably have a uniform average particle diameter.

When the average pore diameter of the porous body 20 is about 30 to 150 nm, the average particle diameter $D_1$ of the fine particles 10 is preferably 100 nm or more, more preferably 150 nm or more. When the substrate protein 25 is an antibody and the average pore diameter of the porous body 20 is about 50 nm to 100 nm, the average particle diameter of the fine particles 10 is preferably 120 nm or more, more preferably 150 nm or more, particularly preferably 170 nm or more. The upper limit of the average particle diameter $D_1$ of the fine particles 10 is not particularly limited, but is preferably 1 μm or less, more preferably 500 nm or less, further preferably 300 nm or less, from the viewpoint of improving the efficiency of protease proteolysis.

The material of the fine particles 10 is not particularly limited as long as the protease can be immobilized on the surface thereof, and a metal, a resin, or the like is appropriately used. Alternatively, a material obtained by coating the surface of a metal with a resin, a material obtained by coating the surface of a resin with a metal, or the like may be used.

The fine particles 10 preferably have a surface capable of suppressing nonspecific protein adsorption and of selectively immobilizing the protease thereon. For example, as shown in FIG. 1, fine particles whose surface is modified by a spacer 11 that can specifically bind with the protease are appropriately used. The spacer is preferably one that can bind with the protease and does not deactivate the protease.

Further, from the viewpoint of controlling the range of accessibility of the protease 15 immobilized on the surface of the fine particles 10, the spacer 11 preferably has a small molecular diameter. The molecular diameter of the spacer is preferably 5 nm or less, more preferably 3 nm or less, further preferably 2 nm or less. Further, the molecular weight of the spacer is preferably 2000 or less, more preferably 1500 or less, further preferably 1000 or less, particularly preferably 800 or less. The spacer molecule that has a molecular diameter in the above range and is capable of immobilizing the protease is preferably non-protein and preferably has a functional group such as an amino group, an amide group, an ester group, an epoxy group, a carboxyl group, biotin, avidin, or a chelate. For example, the spacer preferably used to immobilize trypsin has an ester group. Further, a molecule having an activated ester group is also preferably used as the spacer to improve the efficiency of protease immobilization.

In an aspect of the present invention, commercially-available fine particles modified with a spacer molecule may also be used. For example, fine particles modified with a spacer molecule having an ester group activated by N-hydroxysuccinimide are commercially available as fine particles for affinity purification under the trade name of "FG beads NHS".

Preparation of Protease-Immobilized Fine Particles

A method for immobilizing the protease 15 on the surface of the fine particles 10 is not particularly limited, and an appropriate method can be adopted depending on the properties of the protease and of the fine particles (or the spacer molecule modifying the surface of the fine particles) etc. For example, when trypsin is immobilized on the surface of the fine particles modified with the spacer, a suspension of the fine particles and a solution containing trypsin are mixed together. In this way, the protease can be immobilized on the surface of the fine particles.

After the protease is immobilized on the surface of the fine particles, active portions not binding with the protease on the surface of the fine particles are preferably deactivated. For example, if the spacer molecule not having the protease immobilized thereon is present on the surface of the fine particles, there is a case where a problem that the unbound spacer molecule binds with an impurity or the like in a sample so that protease proteolysis is adversely affected, a problem that peptide fragments produced by protease proteolysis are immobilized on the fine particles, or the like occurs. Such a problem is suppressed by blocking the unbound spacer after the immobilization of the protease. The deactivation of the active portions not binding with the protease is preferably performed by chemical modification. For example, an activated ester group is deactivated by forming an amide bond through a reaction with an amine.

Protease Proteolysis

The substrate protein is subjected to protease proteolysis by bringing the porous body 20 having the substrate protein 25 immobilized thereon and the fine particles 10 having the protease 15 immobilized on the surface thereof into contact with each other in a liquid so that peptide fragments are produced.

In an aspect of the present invention, the condition of the protease proteolysis are not particularly limited, and conditions similar to those of general protease digestion can be appropriately adopted. For example, the protease proteolysis is preferably performed by incubation in a buffer solution having a pH adjusted to about the optimum pH value of the protease at a temperature of usually about 37° C. for about 4 hours to 20 hours.

The quantitative mixing ratio between the porous body having the substrate protein immobilized thereon and the fine particles having the protease immobilized on the surface thereof is not particularly limited, either, and may be set so that the amount of the protease becomes appropriate for the amount of the substrate protein. It is to be noted that protease digestion is generally performed under a condition where the ratio (weight ratio) of substrate protein:protease=about 100:1 to 20:1. On the other hand, in an aspect of the present invention, the amount of the protease is preferably larger than that used in general protease digestion because the access between the substrate protein and the protease is physically limited due to the combined use of the porous body and the fine particles. For example, the ratio of substrate protein:protease is preferably about 30:1 to 3:1, more preferably about 15:1 to 4:1, further preferably about 10:1 to 5:1.

In general, when an antibody in a biological sample such as blood is subjected to selective protease digestion, the protease digestion needs to be performed after the sample is first mixed with particles having Protein G or the like immobilized thereon to immobilize the antibody to the particles, impurities are removed, and then the antibody is eluted from the particles and then denatured with urea or guanidine. In the method according to the present invention, in contrast, protease proteolysis is performed in a state where the antibody is kept immobilized on the porous body. Further, peptide fragments produced by protease proteolysis are present in a liquid phase, and therefore peptide fragments of the Fab domain of the antibody can be site-selectively obtained without performing elution or denaturation of the antibody. In this way, in the method according to an aspect of the present invention, peptide fragments can be site-selectively recovered by simpler operation as compared to a conventional method.

Kit for Preparing Peptide Fragments

Peptide fragments may be prepared using a previously-prepared kit for preparing peptide fragments according to an aspect of the present invention. The kit for preparing peptide fragments according to an aspect of the present invention includes a porous body having pores capable of immobilizing a substrate protein and fine particles capable of immobilizing a protease on the surface thereof. The kit may further include a protease. The fine particles may be provided in a state where a protease is immobilized on the surface thereof.

Figure 3:
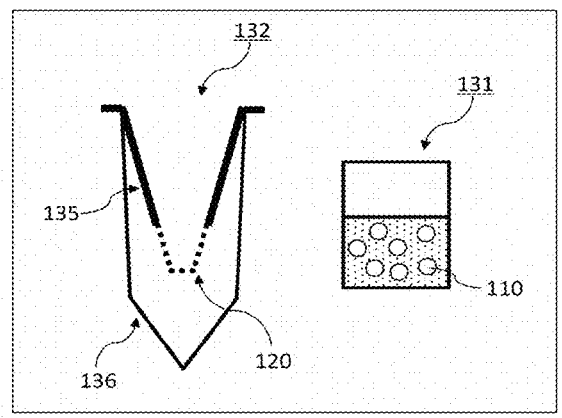
FIG. 3 is a schematic diagram of one embodiment of a kit for preparing peptide fragments.

FIG. 3 is a diagram showing one embodiment of the kit for preparing peptide fragments according to an aspect of the present invention. In FIG. 3, fine particles 110 capable of immobilizing a protease on the surface thereof are provided as a suspension 131. The kit may further include a protease. The fine particles 110 may be provided in a state where a protease is immobilized on the surface thereof. A spin column 132 includes an inner container 135 and an outer container 136, and they are structured so as to be detachably attached to each other. At the bottom of the inner container 135, a porous membrane 120 is provided which has pores capable of immobilizing a substrate protein. The porous membrane 120 has such a pore diameter in order that a liquid is prevented from permeating the porous membrane 120 at an ordinary pressure.

When peptide fragments are prepared using such a spin column, a sample (e.g., a specimen such as blood) containing a substrate protein is first placed in the inner container 135 of the spin column to bring the sample into contact with the porous membrane. If necessary, the container may be shaken to bring the sample into uniform contact with the porous membrane. This operation allows the substrate protein, such as an antibody, to be immobilized in the pores of the porous membrane 120.

The sample liquid after immobilization of the substrate protein on the porous membrane is preferably discharged from the inner container 135. The liquid may be discharged from the opening of the inner container by manipulation such as pipetting or may be discharged from the bottom of the inner container through the porous membrane by centrifugation or the like. Then, if necessary, washing is performed with an appropriate solution.

The fine particles 110 having a protease immobilized on the surface thereof are added to the inner container 135 provided with the porous membrane 120 having the substrate protein immobilized thereon. As described above, the protease may previously be immobilized on the fine particles or may be immobilized on the surface of the fine particles just before use.

If necessary, a solution, such as a buffer, may further be added for the purpose of, for example, optimizing the conditions of protease proteolysis. The substrate protein immobilized on the porous membrane 120 in the inner container is proteolyzed by the protease immobilized on the surface of the fine particles 110. As described above, the conditions of protease proteolysis can be appropriately set. Peptide fragments produced by protease proteolysis migrate into the liquid phase.

The peptide fragments produced by site-selectively proteolyzing the substrate protein are obtained by recovering the liquid phase after protease proteolysis. A method for recovering the liquid phase is not particularly limited. The liquid phase can be simply recovered by centrifugation. In this case, the liquid phase is discharged from the bottom of the inner container 135 through the porous membrane and recovered in the outer container 136. Then, operation such as washing or elution may be performed for the purpose of, for example, elution of the peptide fragments held in the pores of the porous membrane.

As described above, the use of the kit makes it possible to more simply perform the operation of preparing peptide fragments according to an aspect of the present invention and to easily automate the operation using a device. Particularly, trypsin or the like can maintain its activity even in a state where it is immobilized on the surface of the fine particles. Therefore, the operation of preparing peptide fragments can be further simplified by providing, as the component of the kit, a protease in a state where it is immobilized on the surface of the fine particles.

Analysis

A sample containing the peptide fragments obtained above can be analyzed by chromatography or mass spectrometry to identify or quantitate the substrate protein. In an aspect of the present invention, the substrate protein is subjected to site-selective protease treatment, and therefore the number of types of peptide fragments contained in a sample is reduced. Therefore, the conditions of analysis by mass spectrometry or the like can be easily set. If necessary, the sample used for analysis may be subjected to pretreatment, such as desalting, solubilization, extraction, concentration, or drying, before analysis.

Mass spectrometry is suitable for identification or quantitation of the substrate protein from the peptide fragments produced by protease proteolysis. Mass spectrometry can determine the amino acid sequences of peptide fragments, and therefore can determine whether or not the peptide fragments are derived from a specific protein such as an antibody. Further, the concentrations of the peptide fragments in the sample can be determined based on peak intensities.

An ionization method used in mass spectrometry is not particularly limited, and may be, for example, electron ionization (EI), chemical ionization (CI), field desorption (FD), fast atom bombardment (FAB), matrix-assisted laser desorption ionization (MALDI), or electrospray ionization (ESI). A method for analyzing the ionized sample is not particularly limited, and may be appropriately determined depending on the ionization method used. Examples of the method include a magnetic deflection method, a quadrupole (Q) method, an ion trap (IT) method, a time-of-flight (TOF) method, and a Fourier transform ion cyclotron resonance (FT-ICR) method. Alternatively, a triple quadrupole mass spectrometer or the like may be used to perform MS/MS analysis or hybrid mass spectrometry such as $MS^3$ or higher-order MS.

For the purpose of, for example, more reliably separating the peptide fragments to improve the accuracy of analysis, the sample may be separated and concentrated by liquid chromatography (LC), solid phase extraction (SPE), or the like before subjected to mass spectrometry. When the sample is separated by LC, LC/MS including LC prior to mass spectrometry may be used so that an eluate from LC is directly ionized and subjected to mass spectrometry. The sample may be analyzed by LC/MS/MS or LC/MS. that is a combination of LC and tandem mass spectrometry. The eluate from LC may be once fractionated before subjected to mass spectrometry. A column for LC or a carrier for SPE is not particularly limited and may be appropriately selected. For example, a hydrophobic column, such as C30, C18, C8, or C4, generally used for peptide analysis or a carrier for hydrophilic affinity chromatography may be used.

Existing databases may be used to identify the protein, such as an antibody, based on the result of mass spectrometry. In an aspect of the present invention, peptide fragments obtained by site-selective protease proteolysis of the substrate protein such as an antibody are used, and therefore a hit rate in database search or data accuracy is increased. Further, the substrate protein can also be identified by identifying the amino acid sequences of the peptide fragments by hybrid mass spectrometry or the like. For example, when the substrate protein is an antibody, the antibody can be identified by determining the sequence of a peptide fragment containing at least part of the amino acid sequence of a complementarity-determining region (CDR) having an amino acid sequence specific to the antibody.

When the antibody is detected or quantitated based on the result of detection of a specific peptide fragment containing the sequence of CDR, the peptide to be detected preferably has about 5 to 30 amino acid residues, more preferably about 7 to 25 amino acid residues. If the number of amino acid residues is excessively small, the peptide to be detected is difficult to distinguish from peptide fragments derived from impurities or other sites of the same protein, which may cause false detection etc. On the other hand, if the number of amino acid residues is excessively large, in such cases where detection becomes difficult or quantitativity is reduced for the reason that ionization becomes difficult or the like.

When the concentration of the substrate protein is quantitated, the amount of the substrate protein can be calculated based on the peak areas or peak intensities of detected peptide fragment ions (in the case of hybrid MS, fragment ions obtained by fragmentation of peptide fragment ions). For example, the concentrations of the peptide fragments in the sample are calculated based on the association between a previously-determined calibration curve and peak areas, the association between peak areas derived from an internal standard added to the sample and peak areas derived from the sample, or the like, and the amount or concentration of the substrate protein is calculated based on the concentration of the peptide fragments.

As described above, according to an aspect of the present invention, both the substrate protein and the protease are immobilized on solid phases to physically control the access between them so that a specific site in the substrate protein can be subjected to site-selective protease proteolysis. The peptide fragments so obtained can be analyzed by a method such as mass spectrometry, and therefore the protein in the sample can be identified or quantitated without complicated processes.

The method according to an aspect of the present invention is particularly suitable for detection or quantitation of an antibody. The sequence or amount of a peptide fragment containing the amino acid sequence of a complementarity determining region can be determined by mass spectrometry of a peptide fragment sample obtained by subjecting the Fab region of an antibody to selective protease proteolysis. Further, the method according to an aspect of the present invention can be implemented by simple operation, can ensure reproducibility or quantitativity, and can also be automated. Therefore, the method can be applied also to fundamental research such as pharmacokinetic analysis, interactive analysis using antigen-antibody reaction, various interactome analysis, and identification of immunoprecipitated proteins. In addition, the method according to an aspect of the present invention can be expected to be applied to sequencing analysis of biomolecular drugs such as antibody drugs, quality assurance, confirmation of identity of generic drugs, etc.

EXAMPLES

Hereinbelow, experimental examples will be described in which a peptide fragment sample obtained by subjecting human immunoglobulin G (IgG) or trastuzumab (trade name: Herceptin) to protease proteolysis by the method according to an aspect of the present invention was subjected to mass spectrometry. It is to be noted that the present invention is not limited to the following examples.

In the following description, % represents % by weight unless otherwise specified. Reagents and the like used in the experimental examples are as follows.

Trypsin (sequencing grade, promega)
Lysyl endopeptidase (mass spectrometry grade, Wako Pure Chemical Industries, Ltd.)
2-Morpholinoethanesulfonic acid (MES, DOJINDO LABORATORIES)
2-[4-(2-Hydroxyethyl)-1-piperazinyl]ethanesulfonic acid (HEPES, DOJINDO LABORATORIES)
Tris(hydroxymethyl)aminomethane (Tris, Wako Pure Chemical Industries, Ltd.)

Reagents and the like other than those listed above, such as organic solvents, were purchased from Wako Pure Chemical Industries, Ltd.

The following buffer solutions whose pH values were adjusted with a precise pH meter were used.

MES buffer: 25 mM MES-NaOH, pH 5.5
HEPES buffer: 25 mM HEPES-NaOH, pH 7.0 Ethanolamine buffer: 1M ethanolamine-HCl, pH 8.0
Tris buffer: 25 mM Tris-HCl, pH 8.0

<Preparation of Antibody-Immobilized Porous Body>
A suspension of porous resin beads having Protein G bound to the surfaces thereof (Pierce Biotechnology, Protein G UltraLink resin, average particle diameter: 100 µm, pore diameter: 50 to 100 nm) of 5 µL was added to 200 µL of MES buffer, and then an antibody solution was added thereto. Then, the resulting mixture was gently stirred at room temperature for about 1 hour so that an antibody was immobilized by binding to Protein G on the surfaces of the resin beads. Then, the resin beads were precipitated by centrifugation at 4° C. (15000 rpm, 1 min) to remove the supernatant. Then, washing with Tris buffer and centrifugation were repeated twice, and the porous beads were suspended in Tris buffer. (200 µL). As the antibody solution, a human immonglobulin (IgG) solution (10 mg/mL, Sigma-Aldrich) or a trastuzumab (Herceptin, 20 mg/mL, CHUGAI PHARMACEUTICAL CO., LTD.) solution was used.

<Preparation of Protease-Immobilized Fine Particles>
Nanometer-sized fine particles for protease immobilization (TAMAGAWA SEIKI CO., LTD., FG beads NHS) were used which were obtained by modifying the surfaces of fine particles having an average particle diameter of 190 nm with a spacer whose carboxyl group was activated by N-hydroxysuccinimide (see the following chemical formula, wherein L represents a binding site that binds to the surface of the fine particles), spacer length: 1 nm).

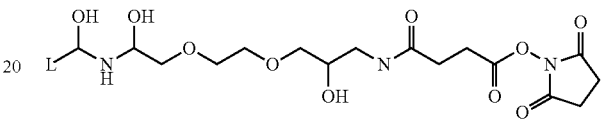

Isopropanol suspension of FG beads of 50 µL was centrifuged at 4° C. (15000 rpm, 5 min) to precipitate the fine particles and remove the supernatant. Then, the fine particles were washed with methanol. A solution containing 50 µg of protease was dissolved in 200 µL of HEPES buffer, and the resulting solution was added to the fine particles to obtain a suspension in which the fine particles were suspended. Herein, the suspension of the fine particles was performed by ultrasonic treatment for a few seconds to prevent the increase in temperature of the suspension.

The fine particle suspension was stirred at 4° C. for 30 minutes and then centrifuged at 4° C. (15000 rpm, 5 min) to precipitate the fine particles and remove the supernatant. Then, 200 µL of ethanolamine buffer was added to suspend the beads, and the resulting suspension was stirred at 4° C. for 30 minutes to block redundant N-hydroxysuccinimide groups on the surface of the fine particles with ethanolamine. Then, the fine particles were precipitated by centrifugation at 4° C. (15000 rpm, 5 min) to remove the supernatant. Then, washing with Tris buffer and centrifugation were repeated twice, and the fine particles were suspended in Tris buffer (100 µL). The protease concentration of the suspension was 0.5 µg/µL.

Experiment 1

Determination of Amount of Antibody Immobilized on Porous Body

In the preparation of the antibody-immobilized porous body, the amount of the Protein G-binding resin bead suspension per 100 µg of IgG was changed in the range of 0 to 20 µL, and the resulting supernatant was analyzed by SDS-PAGE electrophoresis. The approximate amount of unbound IgG remaining in the supernatant (residual amount of antibody) was determined from the number of pixels per band in the resulting electrophoretic pattern. The residual amount of antibody tended to reduce as the amount of the Protein G-binding resin beads increased. When the amount of the Protein G-binding resin beads was 10 µL, the residual amount of antibody was about 3%, from which it was confirmed that specifications given in the catalog of the Protein G-binding resin beads were almost reproduced (data not shown).

Experiment 2

Examination of Quantitative Ratio Between Antibody and Protease

The IgG-immobilized porous body suspension (Protein G-IgG) and the protease-immobilized fine particles (FG beads-Trypsin) were mixed together, and the resulting mixture was gently stirred at 37° C. for 15 hours to perform protease proteolysis. Then, the resin was precipitated by centrifugation at 4° C. (15000 rpm, 5 min) to recover the liquid phase (supernatant). The above experiment was performed by changing the amount of the protease-immobilized fine particles so that the amount of the protease was 5 µg (Level 1), 10 µg (Level 2), or 25 µg (Level 3). In the case of Levels 4 to 6, the experiment was performed in the same manner except that a porous body on which no IgG was immobilized (Protein G UltraLink resin) was directly used instead of the IgG-immobilized porous body suspension. Further, in the case of Levels 7 and 8, only the protease-immobilized fine particles (FG beads-Trypsin) were incubated at 37° C. for 15 hours without using a porous body.

Figure 4:
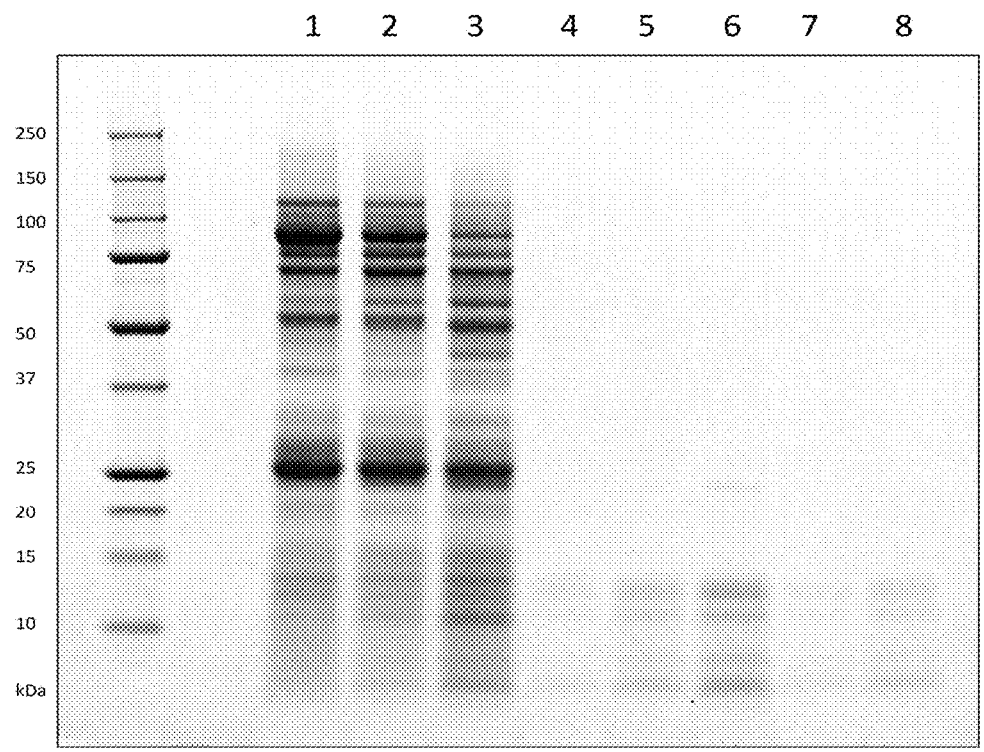
FIG. 4 shows electrophoretic patterns obtained in an experiment for examining the quantitative ratio of a protease.

The levels of the above experiments are shown in Table 2. The weight (µg) shown in Table 2 represents the amount of the protein (IgG or trypsin) in a sample. The SDS-PAGE electrophoretic patterns of the obtained supernatants are shown in FIG. 4. In FIG. 4, the leftmost lane is a molecular weight marker.

TABLE 2

|   | Protein G-IgG (µg) | FG beads-Trypsin (µg) |
|---|---|---|
| 1 | 100 | 5 |
| 2 | 100 | 10 |
| 3 | 100 | 25 |
| 4 | Protein G only | 5 |
| 5 | Protein G only | 10 |
| 6 | Protein G only | 25 |
| 7 | — | 5 |
| 8 | — | 10 |

(Mass Spectrometry)

The supernatants of Levels 1 to 6 were analyzed by MALDI-TOFMS (AXIMA Resonance MALDI-QIT TOF MS, SHIMADZU CORPORATION). First, trifluoroacetic acid was added to 20 µL of the supernatant so that its final concentration was 0.5%, and the resulting mixture was purified using a hydrophobic resin-packed tip (Millipore, ZipTip uC18). Then, elution was performed twice with 1 µL of an eluant. The resulting eluate was directly applied onto a MALDI stainless steel target and air-dried in a clean bench. After the air drying, 1 µL of a 10 mg/mL 2,5-dihydroxybenzoic acid solution (DHBA, SHIMADZU GLC Ltd., water/acetonitrile=50/50) was layered thereon to perform mass spectrometry. m/z of the apparatus was calibrated with Angiotensin II peptide (m/z=1046.54, Sigma-Aldrich) and ACTH fragment peptide (m/z=2465.20, Sigma-Aldrich). The resulting MS spectra are shown in FIG. 5.

All the bands of Levels 4 to 6 shown in FIG. 4 were the same as those of Levels 7 and 8. Further, all the peaks at m/z=842, 1045, 2211, and 2283 detected in the case of Levels 4 to 6 shown in FIG. 5 are derived from fragments produced by autolysis of trypsin. As can be seen from these results, Protein G is not proteolyzed when the protease-immobilized fine particles and the Protein G-binding porous body are brought into contact with each other. The reason for this is considered to be that the pore diameter of the porous body is smaller than the particle diameter of the protease-immobilized fine particles, and therefore trypsin immobilized on the surface of the fine particles cannot have accessibility to Protein G in the pores.

Figure 5:
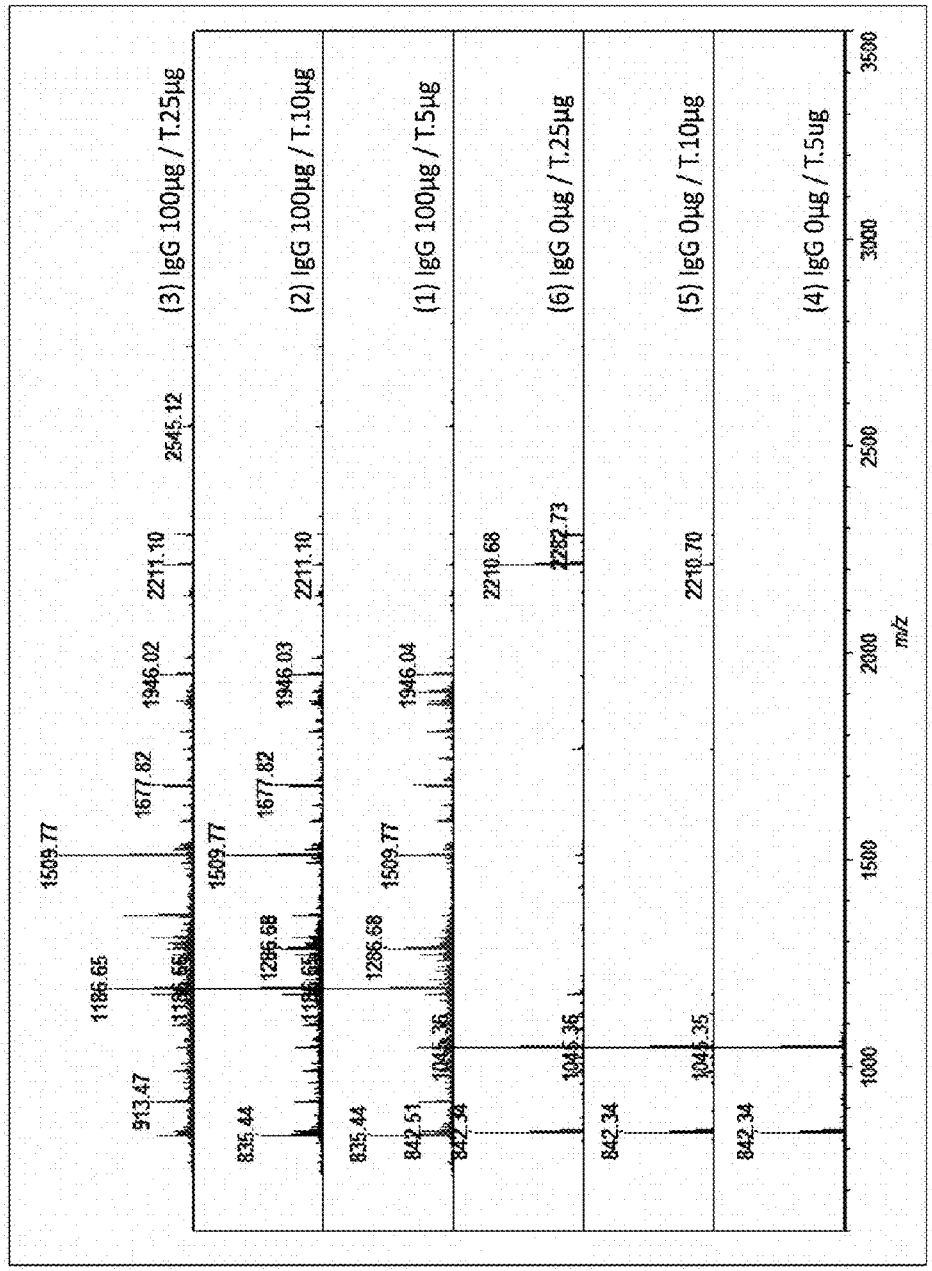
FIG. 5 shows mass spectra (MALDI-TOFMS) obtained in the experiment for examining the quantitative ratio of a protease.

As shown in FIG. 5, in the case of Levels 1 to 3, peaks other than the peaks of fragments produced by autolysis of trypsin were detected at m/z=835, 913, 1187, 1287, 1510, 1678, and 1946, and were all confirmed to be derived from peptide fragments produced by trypsin proteolysis of IgG. This result showed that IgG could be selectively proteolyzed without proteolyzing Protein G immobilized on the porous body by bringing the IgG-immobilized porous and the trypsin-immobilized fine particles into contact with each other.

As can be seen from the comparison among the electrophoretic patterns of Levels 1 to 3 shown in FIG. 4, as the amount of trypsin increases, high-molecular weight bands reduce, that is, the proteolysis reaction of the antibody more efficiently proceeds. On the other hand, as the amount of trypsin increases, autolysis becomes more pronounced. Based on these results, Level 2 (ratio of substrate:enzyme=10:1) was set as a standard condition to examine another condition that will be described later.

It is to be noted that protease digestion is generally performed under the condition where the ratio of substrate protein:protease=100:1 to 20:1. In the method according to an aspect of the present invention, the accessibility between the substrate protein and the protease is physically limited by the combined use of the porous body and the fine particles, and therefore the amount of the protease is larger than that in general protease digestion. For this reason, an optimum substrate-enzyme ratio is estimated to be about 10:1 to 5:1.

Experiment 3

Evaluation of Recovered Peptides Based on Proteolysis Time

The IgG-immobilized porous body suspension (amount of IgG on solid phase: 100 µg) and the protease-immobilized fine particles (amount of trypsin on solid phase: 10 µg) were mixed so that the condition of Level 2 selected in Experiment 2 was satisfied, and the time of proteolysis at 37° C. was set to (1) 15 mins, (2) 45 mins, (3) 90 mins, (4) 180 mins, (5) 360 mins, and (6) 15 hrs (overnight, O/N). Trypsin proteolysis was performed in the same manner as in Experiment 2 except for the above change, and obtained samples were subjected to mass spectrometry. The resulting MS spectra are shown in FIG. 6.

Figure 6:
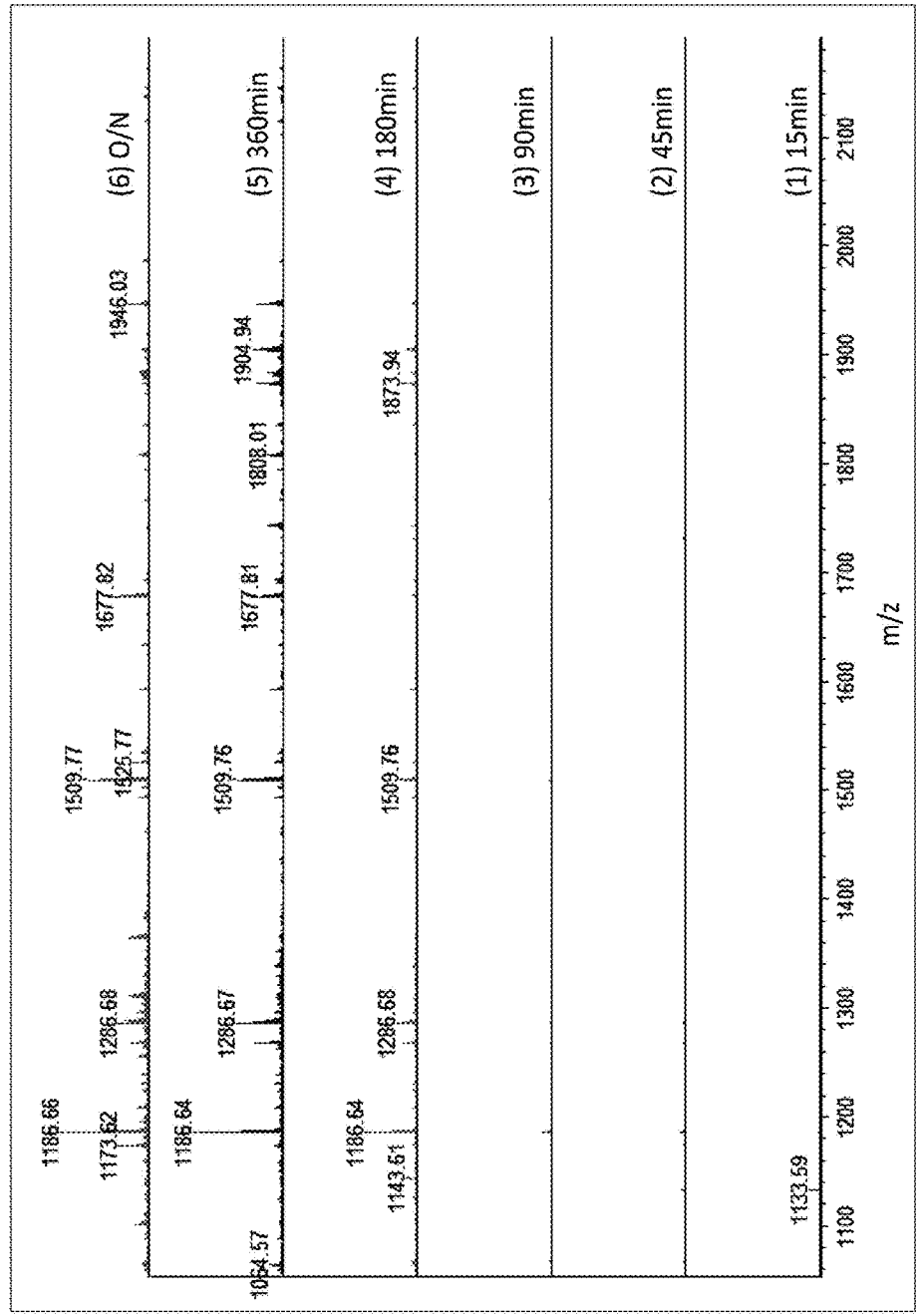
FIG. 6 shows mass spectra (MALDI-TOFMS) obtained in an experiment for examining proteolysis time.

As can be seen from FIG. 6, as the proteolysis time increases, the peaks of peptide fragments increase, that is, the amounts of recovered peptide fragments increase. The recovery rate of peptide fragments was higher in the case of overnight (6) than in the case of 360 min (5). Particularly, accumulation of fragments easily produced by protease proteolysis at m/z=1187, 1510, 1678, etc. tended to be more pronounced. However, these fragments are derived from the C region of the antibody, and therefore do not contribute to the analysis of peptide fragments containing CDR. Therefore, the time of protease proteolysis was set to 6 hrs to make the following study.

Experiment 4

Trypsin Proteolysis and Mass Spectrometry of Trastuzumab

An antibody-immobilized porous body was prepared using Herceptin instead of IgG as an antibody and subjected to trypsin proteolysis under the condition selected in Experiments 2 and 3, that is, under the condition where the amount of the protease-immobilized fine particles per 100 µg of the amount of antibody on solid phase was 10 µg and the proteolysis time was 6 hours. Then, mass spectrometry was performed and database (Mascot server) analysis was performed based on the result of mass spectrometry. As can be seen from FIG. 7, Herceptin (Chain B, X-Ray Structures Of The Antigen-Binding Domains From Three Variants Of Humanized Anti-P185-Her2 Antibody 4d5 And Comparison With Molecular Modeling) is identified with a very high score.

Figure 8:
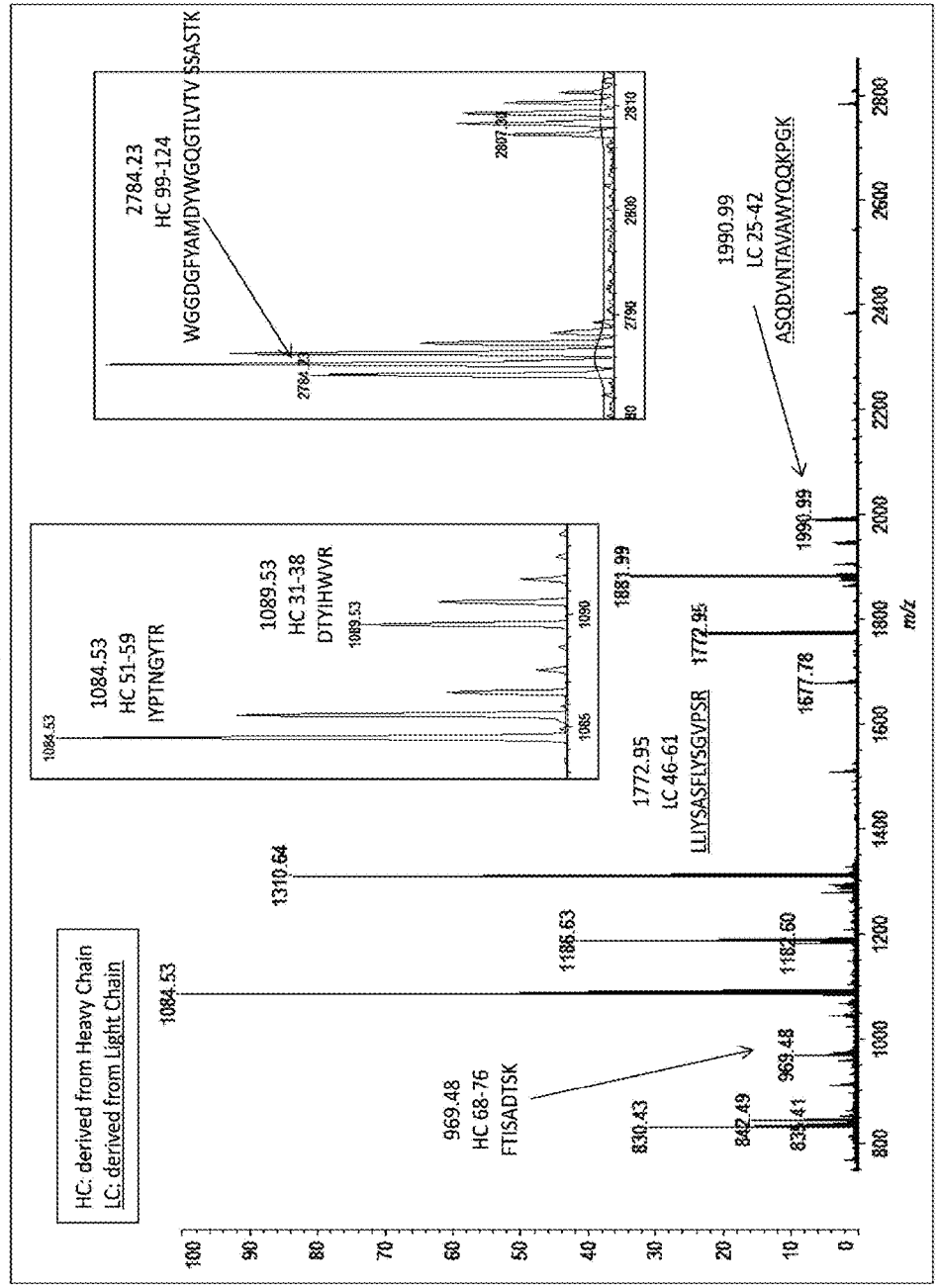
FIG. 8 shows a mass spectrum (MALDI-TOFMS) of tryptic fragments of trastuzumab. The fragments shown in FIG. 8 include FTISADTSK (residues 68-76 of SEQ ID NO: 1), IYPTNGYTR (residues 51-59 of SEQ ID NO: 1), DTYIHWVR (residues 31-38 of SEQ ID NO: 1), WGGDGFYAMDYWGQGTLVTVSSASTK (residues 99-124 of SEQ ID NO: 1), LLIYSASFLYSGVPSR (residues 46-61 of SEQ ID NO: 2), and ASQDVNTAVAWYQQKPGK (residues 25-42 of SEQ ID NO: 2).

In order to confirm that peptide fragments of Herceptin were detected by mass spectrometry, a more detailed analysis was performed in this experiment. FIG. 8 shows the resulting mass spectrum (MALDI-TOFMS).

Figure 9:
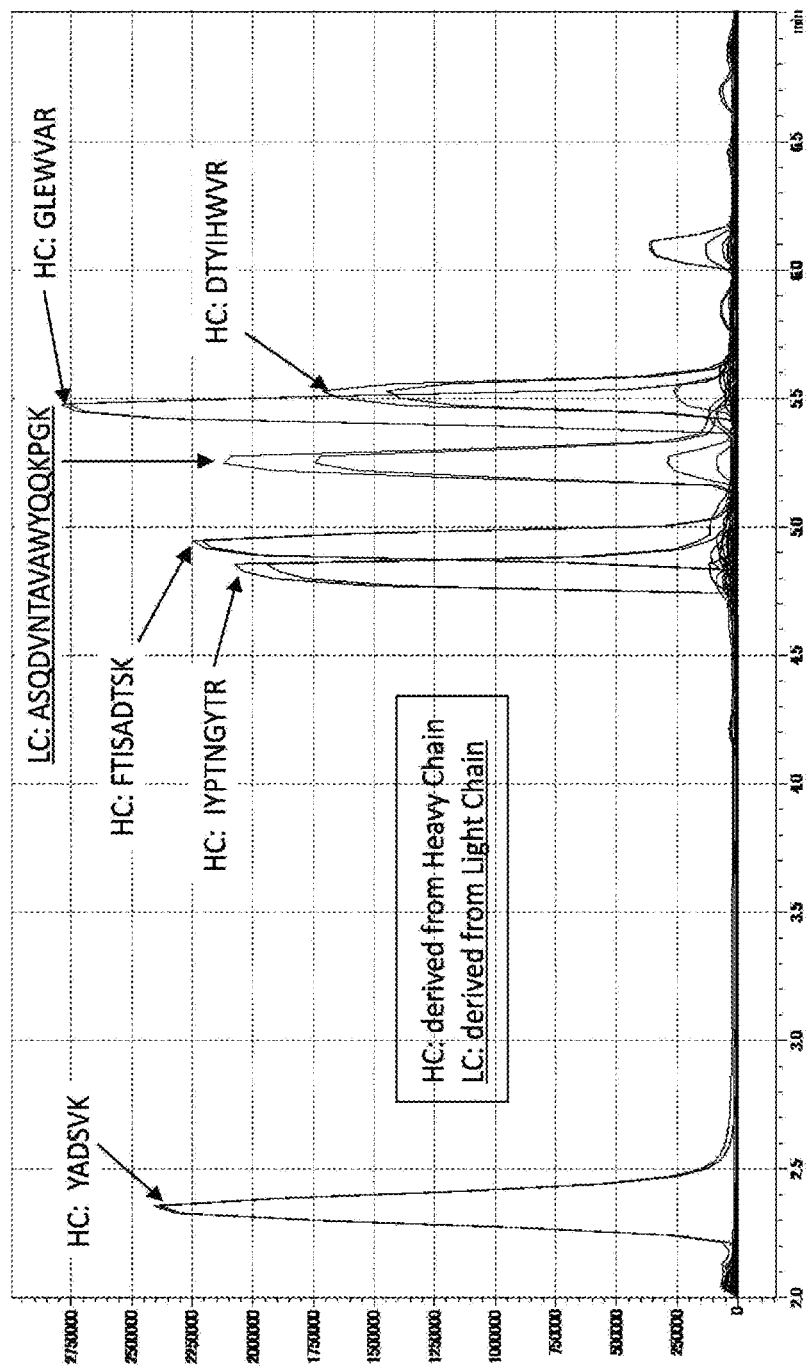
FIG. 9 shows chromatograms of LC-MS analysis of tryptic fragments of trastuzumab. The fragments shown in FIG. 9 include YADSVK (residues 60-65 of SEQ ID NO: 1), FTISADTSK (residues 68-76 of SEQ ID NO: 1), IYPTNGYTR (residues 51-59 of SEQ ID NO: 1), GLEWVAR (residues 44-50 of SEQ ID NO: 1), DTYIHWVR (residues 31-38 of SEQ ID NO: 1), and ASQDVNTAVAWYQQKPGK (residues 25-42 of SEQ ID NO: 2).
Figure 10:
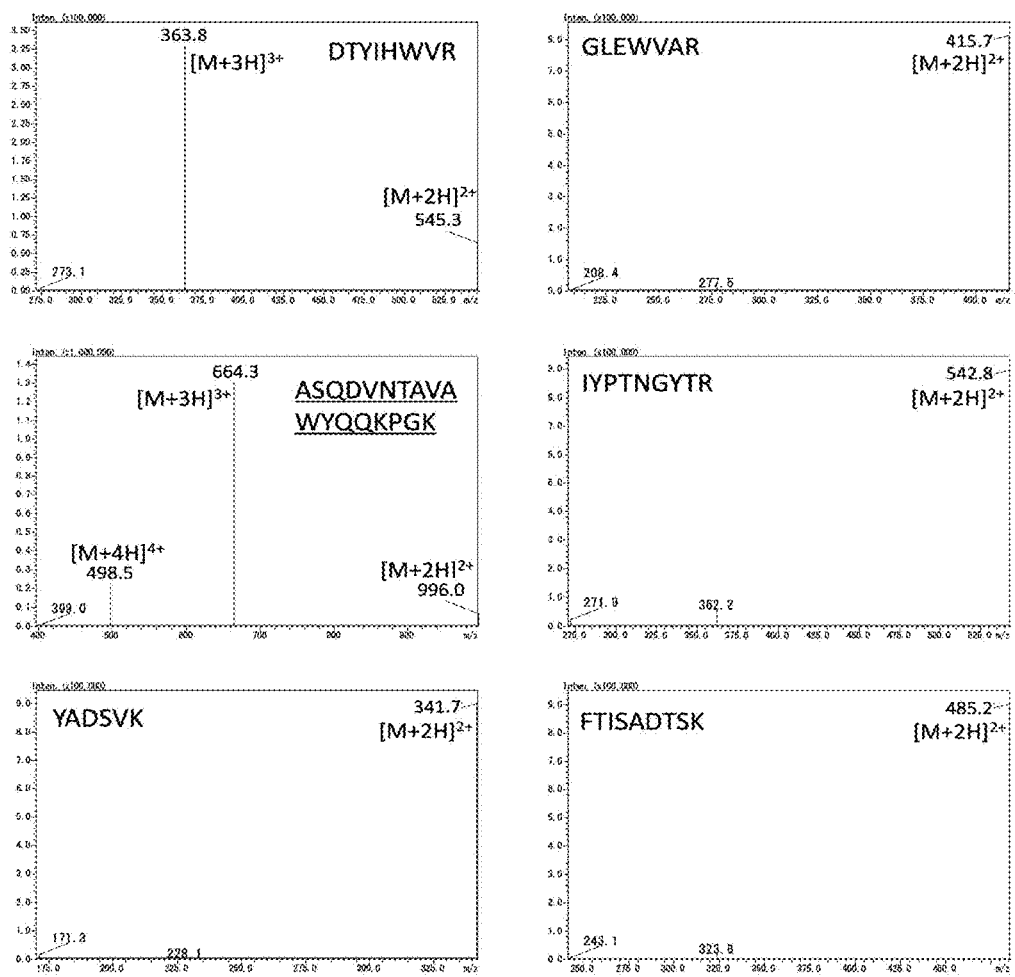
FIG. 10 shows mass spectra (LS-MS) of tryptic fragments of trastuzumab. The fragments shown in FIG. 10 include YADSVK (residues 60-65 of SEQ ID NO: 1), FTISADTSK (residues 68-76 of SEQ ID NO: 1), IYPTNGYTR (residues 51-59 of SEQ ID NO: 1), GLEWVAR (residues 44-50 of SEQ ID NO: 1), DTYIHWVR (residues 31-38 of SEQ ID NO: 1), and ASQDVNTAVAWYQQKPGK (residues 25-42 of SEQ ID NO: 2).

Further, the resulting supernatant after proteolysis was analyzed by LC-MS (LCMS-8080 Triple-quadrupole ultra high-performance liquid chromatography-MS, SHIMADZU CORPORATION). FIG. 9 shows the resulting LC-MS chromatogram and FIG. 10 shows the resulting MS spectra. LC-MS measurement was performed using a sample prepared by adding formic acid to the supernatant to a final concentration of 0.5%, and LC was performed under the following conditions.
<HPLC Solutions>
Solution A: 0.1% formic acid, 1% acetonitrile/aqueous solution
Solution B: 0.1% formic acid, acetonitrile solution
<Column>
ShimPack ODS XR-ODS II (inner diameter: 2 mm, column length: 50 mm)
Column Temperature: 40° C.
Flow Rate: 0.4 mL/min
Injection Amount: 20 µL
<Gradient Program>
0-2 min: % B=0
2-10 min: % B=0-40 gradient
10-11 min: % B=40-98 gradient
11-13 min: % B=98
13-13.5 min: % B=98-0
13.5-15 min: % B=0

Figure 7:
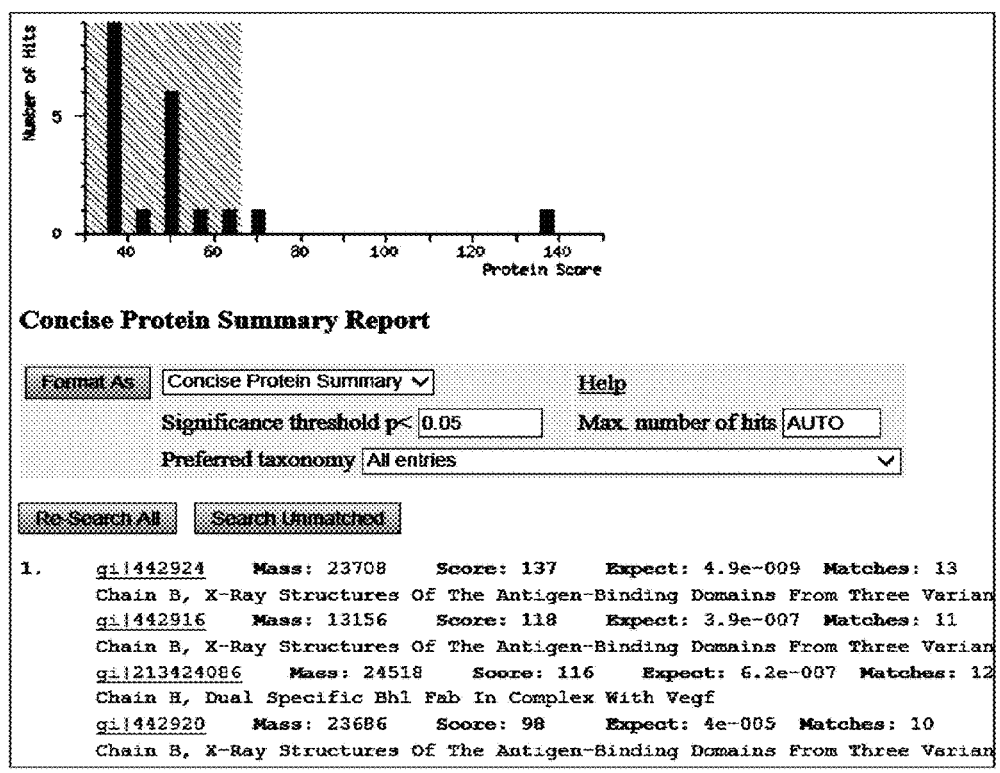
FIG. 7 shows the result of database analysis based on the result of mass spectrometry of tryptic fragments of trastuzumab.

Underlined peptide sequences in the heavy chain (FIG. 11A, SEQ ID No. 1 in Sequence Listing) and light chain (FIG. 11B, SEQ ID No. 2 in Sequence Listing) of trastuzumab were detected and identified by the above mass spectrometry. As can be seen from FIG. 11A, all the CDR1 (SEQ ID No. 3 in Sequence Listing), CDR2 (SEQ ID No. 4 in Sequence Listing), CDR3 (SEQ ID No. 5 in Sequence Listing) of the heavy chain were detected. Further, as shown in FIG. 11B, the CDR1 (SEQ ID No. 6 in Sequence Listing) and CDR2 (SEQ ID No. 7 in Sequence Listing) of the light chain were detected. A tryptic fragment containing the sequence of CDR3 (SEQ ID No. 8 in Sequence Listing) of the light chain has a length of 4 amino acid residues or 37 amino acid residues, and is therefore not suitable for mass spectrometry. This is the reason that the CDR3 of the light chain could not be identified. However, it is considered that a peptide fragment that allows the CDR3 of the light chain to be detected by mass spectrometry can be prepared by changing the type of protease used. Further, in this experiment, 5 out of the total 6 CDRs of the heavy and light chains were detected, although the CDR3 of the light chain could not be detected. Therefore, as shown in FIG. 7, trastuzumab was identified by database analysis.

As can be seen from the above, since the peptide fragments prepared by the method according to an aspect of the present invention are peptide fragments obtained by site-selective protease proteolysis of the antibody, the antibody can be identified by mass spectrometry measurement without the need for setting complicated measurement conditions.

Experiment 5

Study of Mixed Protease Proteolysis

In order to study the applicability of mixed protease proteolysis to a system according to an aspect of the present invention, the experiment of protease proteolysis was performed using trypsin and lysyl endopeptidase (Lys-C) in combination.

An antibody (IgG or Herceptin) was subjected to protease proteolysis in the same manner as in each of the above experimental examples by stirring an antibody-immobilized porous body having 100 µg of the antibody immobilized on Protein G bound thereto and fine particles having 10 µg of protease immobilized thereon at 37° C. for 6 hours. The experiment was performed for both cases where IgG was used as an antibody and where Herceptin was used as an antibody under the condition where the ratio (weight ratio) between trypsin and lysyl endopeptidase was set to (1) 10:0, (2) 9:1, (3) 8:2, and (4) 0:10. The resulting supernatant after proteolysis and the component immobilized on the surface of the porous body were analyzed by SDS-PAGE electrophoresis. The resulting electrophoretic patterns are shown in FIG. 12. In FIG. 12, the leftmost lane is a molecular weight marker.

Figure 13:
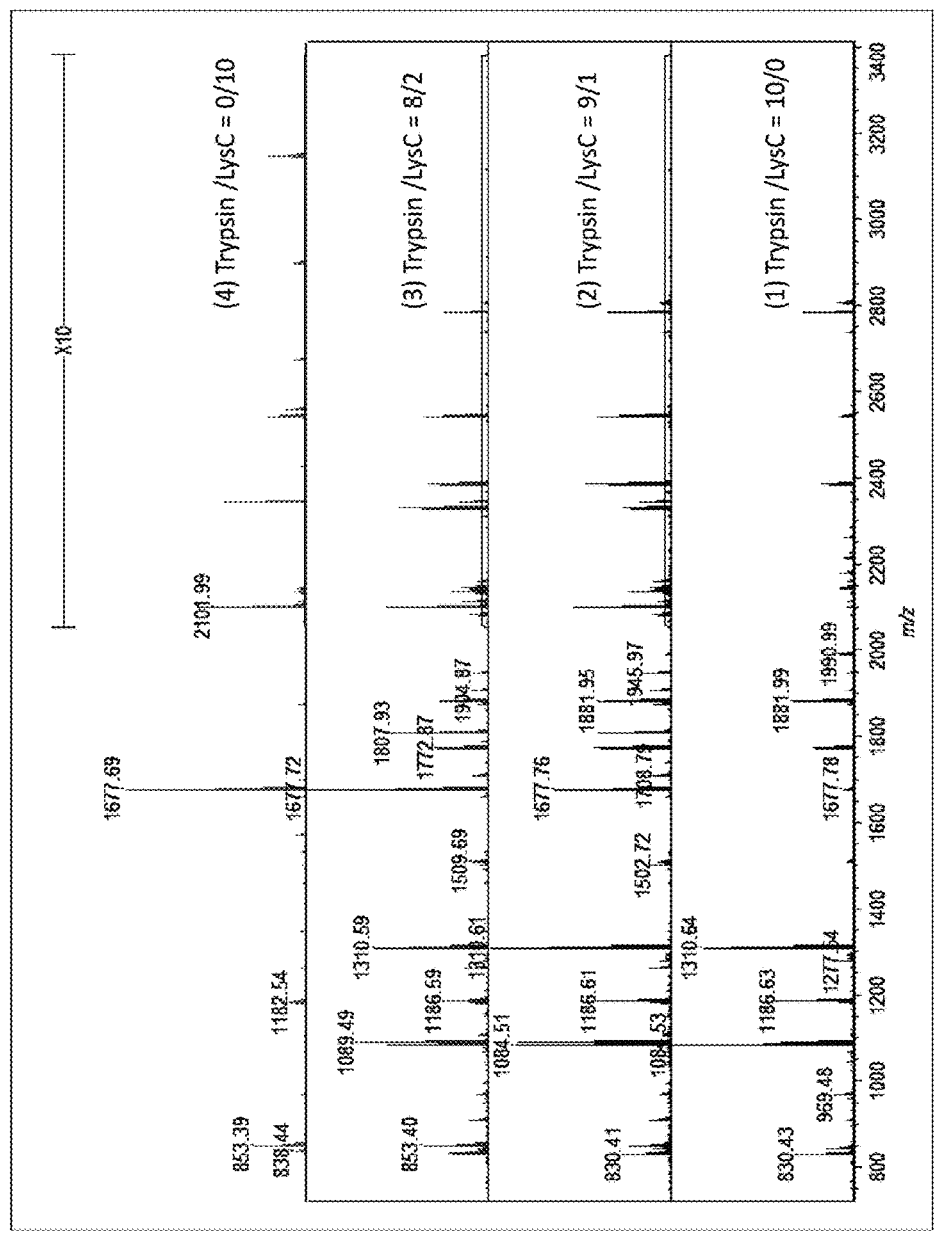
FIG. 13 shows mass spectra (MALDI-TOFMS) obtained in the experiment for studying mixed protease proteolysis.

The supernatants after proteolysis of Levels 1 to 4 obtained when Herceptin was used as an antibody were subjected to mass spectrometry in the same manner as in the above Experiment 2. The resulting MS spectra are shown in FIG. 13. Further, database analysis was performed by Mascot server in the same manner as in Experiment 4 based on the result of mass spectrometry. The database analysis result of Level 1 (trypsin 100%) was the same as that obtained in the above Experiment 4 (FIGS. 7 and 8). The database analysis results of Levels 2 to 4 are as follows (data was not shown).

<Level 2: trypsin lysyl endopeptidase=90:10>
Mixture
gi|442924 Mass: 23708 Score: 117 Expect: 4.9e−007 Matches: 13
Chain B, X-Ray Structures Of The Antigen-Binding Domains From Three
Variants Of Humanized Anti-P185-Her2 Antibody 4d5 And Comparison With Molecular Modeling
gi|184747 Mass: 36012 Score: 64 Expect: 0.11 Matches: 10
immunoglobulin gamma-1 heavy chain constant region (*Homo sapiens*)
<Level 3: trypsin lysyl endopeptidase=80:20>
Mixture
gi|442924 Mass: 23708 Score: 115 Expect: 7.8e−007 Matches: 13
Chain B, X-Ray Structures Of The Antigen-Binding Domains From Three
Variants Of Humanized Anti-P185-Her2 Antibody 4d5 And Comparison With
Molecular Modeling
gi|184747 Mass: 36012 Score: 54 Expect: 1.1 Matches: 9
immunoglobulin gamma-1 heavy chain constant region (*Homo sapiens*)

<Level 4: lysyl endopeptidase 100%>
gi|184747 Mass: 36012 Score: 71 Expect: 0.021 Matches: 8 immunoglobulin gamma-1 heavy chain constant region (*Homo sapiens*)

In the cases of Levels 2 and 3 in which trypsin and lysyl endopeptidase were used in combination, the analysis result showed that the constant region of a human-derived antibody as well as the antigen-binding region of Herceptin were detected. In the case of Level 4 in which lysyl endopeptidase was used alone, the analysis result showed that Herceptin was not detected, and only the constant region of an antibody was dominantly detected.

As can be seen from the electrophoretic patterns shown in FIG. 12, there is a tendency that as the ratio of lysyl endopeptidase increases, the number of peptide fragments in the supernatant and the areas of bands also increase, that is, proteolysis efficiency and peptide recovery rate increase. Further, as shown in FIG. 13, the types or amounts of peptide fragments detected increase as the ratio of lysyl endopeptidase increases. However, most of the peptide fragments newly detected in the case of Levels 2 to 4 are derived from the Fc domain of Herceptin, from which it is found that the site-selectivity of protease proteolysis (i.e., the property of selectively proteolyzing the Fab domain) is reduced.

As can be seen from these results, as the amount of lysyl endopeptidase used increases, the proteolysis efficiency of the antibody increases, but the site-selectivity of protease proteolysis reduces, and therefore the relative production amount of peptide fragments from the V region reduces as the production amount of peptide fragments from the constant region increases so that the accuracy of detection and identification of the antibody tends to reduce. Therefore, from the viewpoint of site-selectively proteolyzing the Fab region of the antibody and specifically detecting CDR by the method according to an aspect of the present invention, trypsin is preferably used alone. When trypsin and lysyl endopeptidase are used in combination, the amount of lysyl endopeptidase mixed is preferably 10% or less.

It is to be noted that site-selective proteolysis was not performed in the case of Level 4 using lysyl endopeptidase alone, whereas CDRs were efficiently detected by database analysis in the case of Level 1 (Experiment 4) using trypsin alone, from which it was found that the V region of the Fab domain was subjected to selective protease proteolysis. It can be said that the above results showed that when the substrate protein was an antibody, the steric access of the protease to the antibody was appropriately controlled by applying an aspect of the present invention using trypsin so that site-selective protease proteolysis could be achieved.

Further, this experiment showed that when trypsin and lysyl endopeptidase were used in combination, each of the proteases did not lose its function and could proteolyze the substrate protein immobilized in the pores. An antibody has a V region at the end of its molecule, and therefore when the amount of used lysyl endopeptidase increases, site-selectivity tends to reduce. However, it was suggested that in the case where another protein was used as a substrate, there was a possibility that site-selectivity or proteolysis efficiency was improved by using a combination of proteases.

As can be seen from the above experimental examples, according to an aspect of the present invention, a peptide fragment sample can be obtained by subjecting a protein, such as an antibody, to site-selective protease proteolysis by a simple method, and the obtained peptide fragment sample is suitable for identification or detection of the protein by mass spectrometry.

The inventors have intensively studied to find that immobilization of both a substrate protein, such as an antibody, and a protease on solid phases makes it possible to achieve site-selective protease proteolysis of the substrate protein.

One aspect of the present invention relates to a method for preparing peptide fragments by proteolyzing a protein with a protease. The method includes a step of proteolyzing a substrate protein with a protease by bringing a porous body in which a substrate protein to be proteolyzed is immobilized in pores thereof and fine particles having a protease immobilized on surface thereof into contact with each other in a liquid (proteolysis step). The porous body on which the substrate protein to be proteolyzed is immobilized in the pores thereof can be obtained by a step of immobilizing a substrate protein to be proteolyzed in pores of a porous body (substrate immobilization step). In an aspect of the present invention, an average particle diameter of the fine particles is preferably larger than an average pore diameter of the porous body.

When the particle diameter of the fine particles is larger than the average pore diameter of the porous body, the protease immobilized on the surface of the fine particles can access the opening portions of the pores of the porous body and their vicinities (the interface between the porous body and the liquid phase and its vicinity), but cannot access the deep parts of the pores. In this way, the accessible region of the protease is physically (spatially) limited, and therefore the protease selectively accesses a specific site of the substrate protein immobilized in the pores of the porous body. This makes it possible to achieve site-selective protease proteolysis (fragmentation) of the substrate protein.

In an aspect of the present invention, a predetermined region of the substrate protein is preferably immobilized on the porous body. In this embodiment, the region immobilized on the porous body is located in the deep parts of the pores so that a region different from the immobilized region is located near the opening portions of the pores. When a region different from the selective proteolysis site of the substrate protein, i.e., a region preferred not to be subjected to protease proteolysis, is immobilized on the porous body, the protease immobilized on the surface of the fine particles accesses the selective proteolysis site of the substrate protein located near the opening portions of the pores so that protease proteolysis is performed. This allows site-selective protease proteolysis at a desired site in the substrate protein.

A linker molecule capable of site-specific interaction with the substrate protein is preferably immobilized in the pores of the porous body. The substrate protein is immobilized in the pores of the porous body preferably through the linker molecule. Examples of the linker molecule used when the substrate protein is an antibody include Protein G and Protein A. Such a linker molecule site-specifically binds with the Fc region of the antibody, and therefore the Fc region of the antibody is immobilized on the porous body so that the Fab region of the antibody is located near the opening portions of the pores. According to this embodiment, the Fab region of the antibody can be subjected to selective protease proteolysis.

When the linker molecule is immobilized in the pores of the porous body, a molecule in which the linker molecule binds with the substrate protein preferably has a size 0.5 times to 1.5 times the average pore diameter of the porous body. Such molecular size adjustment makes it possible to increase the probability of access of the protease immobilized on the surface of the fine particles to the selective cleavage site of the substrate protein, thereby improving the site-selectivity of protease proteolysis.

It is preferred that the surface of the fine particles is modified with a spacer molecule capable of binding with the protease, and the protease is immobilized on the surface of the fine particles through the spacer molecule. The immobilization of the protease through the spacer molecule makes it possible to suppress the detachment of the protease from the surface of the fine particles, thereby improving the site-selectivity of protease proteolysis. Further, the adjustment of molecular size of the spacer makes it possible also to allow the protease to selectively access a desired position in the substrate protein to improve the site-selectivity.

In an aspect of the present invention, the protease to be immobilized on the surface of the fine particles is preferably trypsin or a combination of trypsin and another protease. When the substrate protein is an antibody, trypsin is preferably used alone, or in a combination of proteases. When proteases are used in a combination, the amount of trypsin is preferably 90% or more of the total amount of proteases. Particularly, when the substrate protein is an antibody, the Fab domain tends to be subjected to selective protease proteolysis by using trypsin so that the protease proteolysis of the Fc domain is suppressed.

The average pore diameter of the porous body is preferably about 30 to 150 nm, and the average particle diameter of the fine particles is preferably 100 nm or more. Particularly, when the substrate protein is an antibody and the average pore diameter and the average particle diameter are within the above ranges, the Fab region can be more reliably site-selectively proteolyzed.

Another aspect of the present invention relates to a kit for peptide fragment preparation used for the above method. The peptide fragment preparation kit according to an aspect of the present invention includes a porous body having pores capable of immobilizing a substrate protein, and fine particles capable of immobilizing a protease on surface thereof. The fine particles may be provided in a state where the protease is immobilized on the surface thereof. The porous body of the kit and a sample (e.g., a specimen such as blood) are brought into contact with each other such that the subject substance (substrate protein such as an antibody) in the sample can be immobilized in the pores of the porous body. The substrate protein is subjected to site-selective protease proteolysis by bringing the porous body after immobilization of the substrate protein and the fine particles having the protease immobilized on the surface thereof into contact with each other in a liquid.

Peptide fragments obtained by the above method are analyzed by mass spectrometry or the like, which makes it possible to detect (identify) or quantitate the substrate protein. In the present invention, the substrate protein is subjected to site-selective proteolysis, and therefore the number of types of peptide fragments contained in a measurement sample can be significantly reduced. Therefore, the setting of measurement conditions of mass spectrometry can be simplified, and the accuracy of analysis is also expected to be improved.

For example, when the substrate protein is an antibody, the method according to an aspect of the present invention can achieve site-selective protease proteolysis of the Fab region containing a complementarity determining region, and therefore a peptide fragment containing at least part of the sequence of complementarity determining region of the antibody can be produced as a detection target. The complementarity determining region has an amino acid sequence specific to each antibody. Therefore, the antibody can be detected or quantitated by analyzing the peptide fragment containing the sequence of the complementarity determining region.

According to an aspect of the present invention, a protein, such as an antibody, can be subjected to site-selective protease proteolysis by a simple method to obtain peptide fragments. When the method according to an aspect of the present invention is applied to an antibody, proteolysis of Fc region of the antibody is suppressed, and the Fab region containing CDR is subjected to selective protease proteolysis, and therefore the concentration of the peptide fragment containing the amino acid sequence of CDR, which is important for identification of the antibody, in a sample is increased.

The method according to an aspect of the present invention makes it possible to significantly reduce the number of types of peptides contained in a measurement sample. Therefore, the setting of conditions of mass spectrometry can be simplified, and the accuracy of analysis can also be expected to be improved. The concentration of an antibody drug in blood can also be quantitated by analyzing obtained peptide fragments. Therefore, the method according to an aspect of the present invention can also be applied as a pretreatment method for a system for measuring the concentration of an antibody drug in a preclinical or clinical trial.

Further, the method according to an aspect of the present invention can be applied not only to antibody drugs but also to many proteins, and therefore can be expected to be extensively applied to pharmaceutical industry. In addition, the method according to an aspect of the present invention can also be expected to be applied, for example, in the field of fundamental research such as interactive analysis of biomolecules.

Obviously, numerous modifications and variations of the present invention are possible in light of the above teachings. It is therefore to be understood that within the scope of the appended claims, the invention may be practiced otherwise than as specifically described herein.

What is claimed is:

1. A kit for proteolyzing a protein, comprising:
at least one porous body having a plurality of pores in which a protein is to be immobilized; and
a plurality of particles having an average particle diameter larger than an average pore diameter of the pores,
wherein the particles have a surface modified by a spacer such that a protease has been immobilized or is to be immobilized on the surface by specific binding with the spacer,
a ligand molecule is immobilized in the pores of the porous body,
the ligand molecule is capable of site-specifically interacting with and controlling an orientation of the protein to be immobilized, and
the average particle diameter or the average pore diameter is sized such that each of the pores has a limit to the region accessible to the protease, and that the protein is to be immobilized with a tip portion extending into the region accessible to the protease.

2. The kit of claim 1, wherein the particles have a protease immobilized on the surface of the particles modified by the spacer.

3. The kit of claim 1, wherein the average particle diameter of the particles is 100 nm or greater and the average pore diameter of the pores in the porous body is in a range of from 30 nm to 150 nm, provided that the average particle diameter is larger than the average pore diameter.

4. The kit of claim 1, wherein the ligand molecule is capable of site-specifically interacting with Fc domain of an antibody.

5. The kit of claim 1, wherein the ligand molecule is at least one selected from the group consisting of protein A and protein G.

6. The kit of claim 1, wherein the spacer allows specific binding with the protease without deactivating the protease.

7. The kit of claim 1, wherein the spacer has a molecular diameter of 5 nm or less.

8. The kit of claim 1, wherein the spacer has a molecular diameter of 2 nm or less.

9. The kit of claim 1, wherein the spacer has a molecular weight of 2000 or less.

10. The kit of claim 2, wherein the spacer has a molecular weight of 800 or less.

11. The kit of claim 1, wherein the spacer has one of an amino group, an amide group, an ester group, an epoxy group, a carboxyl group, biotin, avidin, and a chelate.

12. The kit of claim 1, wherein the spacer has an ester group.

13. The kit of claim 1, wherein the spacer has an activated ester group.

14. A kit for proteolyzing a protein, comprising:
at least one porous body having a plurality of pores in which a protein is immobilized; and
a plurality of particles having an average particle diameter larger than an average pore diameter of the pores,
wherein the particles have a surface on which a protease has been immobilized,
a ligand molecule is immobilized in the pores of the porous body,
the ligand molecule immobilized in the pores is capable of site-specifically interacting with the immobilized protein, thereby an orientation of the protein immobilized in the pores is controlled,
the average particle diameter or the average pore diameter is sized such that the protease immobilized on the surface of the particles has access to the protein immobilized in the pores of the porous body,
the pores each have a limit to the region accessible to the protease, and
the protein immobilized in the pores has a tip portion extending into the region accessible to the protease.

* * * * *

SEQUENCE LISTING

<160> NUMBER OF SEQ ID NOS: 8

<210> SEQ ID NO 1
<211> LENGTH: 223
<212> TYPE: PRT
<213> ORGANISM: Artificial Sequence
<220> FEATURE:
<223> OTHER INFORMATION: Trastuzumab (genetical recombination)

<400> SEQUENCE: 1

Glu Val Gln Leu Val Glu Ser Gly Gly Gly Leu Val Gln Pro Gly Gly

-continued

```
                1               5                  10                  15
        Ser Leu Arg Leu Ser Cys Ala Ala Ser Gly Phe Asn Ile Lys Asp Thr
                        20                  25                  30

Tyr Ile His Trp Val Arg Gln Ala Pro Gly Lys Gly Leu Glu Trp Val
                        35                  40                  45

Ala Arg Ile Tyr Pro Thr Asn Gly Tyr Thr Arg Tyr Ala Asp Ser Val
                50                  55                  60

Lys Gly Arg Phe Thr Ile Ser Ala Asp Thr Ser Lys Asn Thr Ala Tyr
         65                 70                  75                  80

Leu Gln Met Asn Ser Leu Arg Ala Glu Asp Thr Ala Val Tyr Tyr Cys
                            85                  90                  95

Ser Arg Trp Gly Gly Asp Gly Phe Tyr Ala Met Asp Tyr Trp Gly Gln
                        100                 105                 110

Gly Thr Leu Val Thr Val Ser Ser Ala Ser Thr Lys Gly Pro Ser Val
                        115                 120                 125

Phe Pro Leu Ala Pro Ser Ser Lys Ser Thr Ser Gly Gly Thr Ala Ala
                        130                 135                 140

Leu Gly Cys Leu Val Lys Asp Tyr Phe Pro Glu Pro Val Thr Val Ser
        145                 150                 155                 160

Trp Asn Ser Gly Ala Leu Thr Ser Gly Val His Thr Phe Pro Ala Val
                            165                 170                 175

Leu Gln Ser Ser Gly Leu Tyr Ser Leu Ser Ser Val Val Thr Val Pro
                        180                 185                 190

Ser Ser Ser Leu Gly Thr Gln Thr Tyr Ile Cys Asn Val Asn His Lys
                        195                 200                 205

Pro Ser Asn Thr Lys Val Asp Lys Lys Val Glu Pro Lys Ser Cys
                        210                 215                 220

<210> SEQ ID NO 2
<211> LENGTH: 214
<212> TYPE: PRT
<213> ORGANISM: Artificial Sequence
<220> FEATURE:
<223> OTHER INFORMATION: Trastuzumab (genetical recombination)

<400> SEQUENCE: 2

Asp Ile Gln Met Thr Gln Ser Pro Ser Ser Leu Ser Ala Ser Val Gly
        1               5                   10                  15

Asp Arg Val Thr Ile Thr Cys Arg Ala Ser Gln Asp Val Asn Thr Ala
                        20                  25                  30

Val Ala Trp Tyr Gln Gln Lys Pro Gly Lys Ala Pro Lys Leu Leu Ile
                        35                  40                  45

Tyr Ser Ala Ser Phe Leu Tyr Ser Gly Val Pro Ser Arg Phe Ser Gly
                50                  55                  60

Ser Arg Ser Gly Thr Asp Phe Thr Leu Thr Ile Ser Ser Leu Gln Pro
         65                 70                  75                  80

Glu Asp Phe Ala Thr Tyr Tyr Cys Gln Gln His Tyr Thr Thr Pro Pro
                            85                  90                  95

Thr Phe Gly Gln Gly Thr Lys Val Glu Ile Lys Arg Thr Val Ala Ala
                        100                 105                 110

Pro Ser Val Phe Ile Phe Pro Pro Ser Asp Glu Gln Leu Lys Ser Gly
                        115                 120                 125

Thr Ala Ser Val Val Cys Leu Leu Asn Asn Phe Tyr Pro Arg Glu Ala
                        130                 135                 140

Lys Val Gln Trp Lys Val Asp Asn Ala Leu Gln Ser Gly Asn Ser Gln
```

```
                145                 150                 155                 160
Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 3
<211> LENGTH: 14
<212> TYPE: PRT
<213> ORGANISM: Artificial Sequence
<220> FEATURE:
<223> OTHER INFORMATION: Trastuzumab (genetical recombination)

<400> SEQUENCE: 3

Ser Gly Phe Asn Ile Lys Asp Thr Tyr Ile His Trp Val Arg
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Trastuzumab (genetical recombination)

<400> SEQUENCE: 4

Trp Val Ala Arg Ile Tyr Pro Thr Asn Gly Tyr Thr Arg Tyr
1               5                   10

<210> SEQ ID NO 5
<211> LENGTH: 17
<212> TYPE: PRT
<213> ORGANISM: Artificial Sequence
<220> FEATURE:
<223> OTHER INFORMATION: Trastuzumab (genetical recombination)

<400> SEQUENCE: 5

Tyr Cys Ser Arg Trp Gly Gly Asp Gly Phe Tyr Ala Met Asp Tyr Trp
1               5                   10                  15

Gly

<210> SEQ ID NO 6
<211> LENGTH: 14
<212> TYPE: PRT
<213> ORGANISM: Artificial Sequence
<220> FEATURE:
<223> OTHER INFORMATION: Trastuzumab (genetical recombination)

<400> SEQUENCE: 6

Ala Ser Gln Asp Val Asn Thr Ala Val Ala Trp Tyr Gln Gln
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Trastuzumab (genetical recombination)

<400> SEQUENCE: 7

Leu Ile Tyr Ser Ala Ser Phe Leu Tyr Ser Gly Val Pro Ser
```

```
<210> SEQ ID NO 8
<211> LENGTH: 20
<212> TYPE: PRT
<213> ORGANISM: Artificial Sequence
<220> FEATURE:
<223> OTHER INFORMATION: Trastuzumab (genetical recombination)

<400> SEQUENCE: 8

Tyr Cys Gln Gln His Tyr Thr Thr Pro Pro Thr Phe Gly Gln Gly Thr
1               5                   10                  15

Lys Val Glu Ile
            20
```